US011547861B2

(12) United States Patent
Huertas Fernandez et al.

(10) Patent No.: US 11,547,861 B2
(45) Date of Patent: Jan. 10, 2023

(54) TOOL TO USE IMAGE FOR PROGRAMMING NEUROMODULATION

(71) Applicant: Boston Scientific Neuromodulation Corporation, Valencia, CA (US)

(72) Inventors: Ismael Huertas Fernandez, Madrid (ES); Matthew Lee McDonald, Pasadena, CA (US); Amarpreet Singh Bains, Monrovia, CA (US); Anirudh Joshi, Fremont, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 584 days.

(21) Appl. No.: 16/568,063

(22) Filed: Sep. 11, 2019

(65) Prior Publication Data

US 2020/0101302 A1 Apr. 2, 2020

Related U.S. Application Data

(60) Provisional application No. 62/737,222, filed on Sep. 27, 2018.

(51) Int. Cl.
*A61N 1/372* (2006.01)
*A61B 6/12* (2006.01)
*A61B 6/00* (2006.01)
*A61N 1/05* (2006.01)
*A61N 1/36* (2006.01)
*G16H 30/40* (2018.01)

(52) U.S. Cl.
CPC ............ *A61N 1/37264* (2013.01); *A61B 6/12* (2013.01); *A61B 6/468* (2013.01); *A61B 6/487* (2013.01);

(Continued)

(58) Field of Classification Search
CPC .............. A61N 1/0551; A61N 1/36062; A61N 1/37247; G16H 30/40
See application file for complete search history.

(56) References Cited

U.S. PATENT DOCUMENTS 9,788,756 B2 10/2017 Demmer
2013/0060299 A1 3/2013 Polefko et al.
(Continued)

FOREIGN PATENT DOCUMENTS

| CN | 113056303 A | 6/2021 |
|---|---|---|
| WO | WO-2013090675 A1 | 6/2013 |
| WO | WO-2020068433 A1 | 4/2020 |

OTHER PUBLICATIONS

"Australian Application Serial No. 2019349824, First Examination Report dated Oct. 6, 2021", 3 pgs.
(Continued)

*Primary Examiner* — Joseph M Dietrich
(74) *Attorney, Agent, or Firm* — Schwegman Lundberg & Woessner, P.A.

(57) ABSTRACT

A system may be used with a medical imaging system and a programming system. The medical imaging system may be configured to display a medical image and the programming system may be configured to implement a program used in programming a neuromodulation device. The system may comprise a mobile device having at least one processor, a camera and a user interface including a display. The mobile device may be configured to acquire a displayed medical image from the medical imaging system, determine based on the acquired medical image location data indicative of the position of at least one of the electrodes relative to at least one of the anatomy or at least another one of the electrodes, and provide the location data for use by the program implemented by the programming system.

20 Claims, 17 Drawing Sheets

(52) U.S. Cl.
CPC ....... *A61N 1/0551* (2013.01); *A61N 1/36062* (2017.08); *A61N 1/37247* (2013.01); *G16H 30/40* (2018.01)

(56) References Cited

U.S. PATENT DOCUMENTS

2017/0258419 A1* 9/2017 Li .................. A61N 1/36182
2017/0333134 A1* 11/2017 Wollowick ............... G06T 7/70

OTHER PUBLICATIONS

"Canadian Application Serial No. 3,113,785, Non Final Office Action dated Mar. 9, 2022", 3 pgs.
"European Application Serial No. 19773320.7, Response to Communication pursuant to Rules 161 and 162 filed Nov. 18, 2021", 25 pgs.
"International Application Serial No. PCT/US2019/050665, International Preliminary Report on Patentability dated Apr. 8, 2021", 8 pgs.
"International Application Serial No. PCT/US2019/050665, International Search Report dated Dec. 19, 2019", 3 pgs.
"International Application Serial No. PCT/US2019/050665, Written Opinion dated Dec. 19, 2019", 5 pgs.
"Australian Application Serial No. 2019349824, Response filed Jun. 21, 2022 to First Examination Report dated Oct. 6, 2021", 22 pgs.
"Australian Application Serial No. 2019349824, Subsequent Examiners Report dated Jul. 7, 2022", 3 pgs.
"Canadian Application Serial No. 3,113,785, Response filed Jul. 6, 2022 to Non Final Office Action dated Mar. 9, 2022", 15 pgs.

* cited by examiner

TRANSFER MATRIX A (m x n)

$m$ field potential values due to constituent source #1
$m$ field potential values due to constituent source #2
$m$ field potential values due to constituent source #3

⋮

$m$ field potential values due to constituent source #n

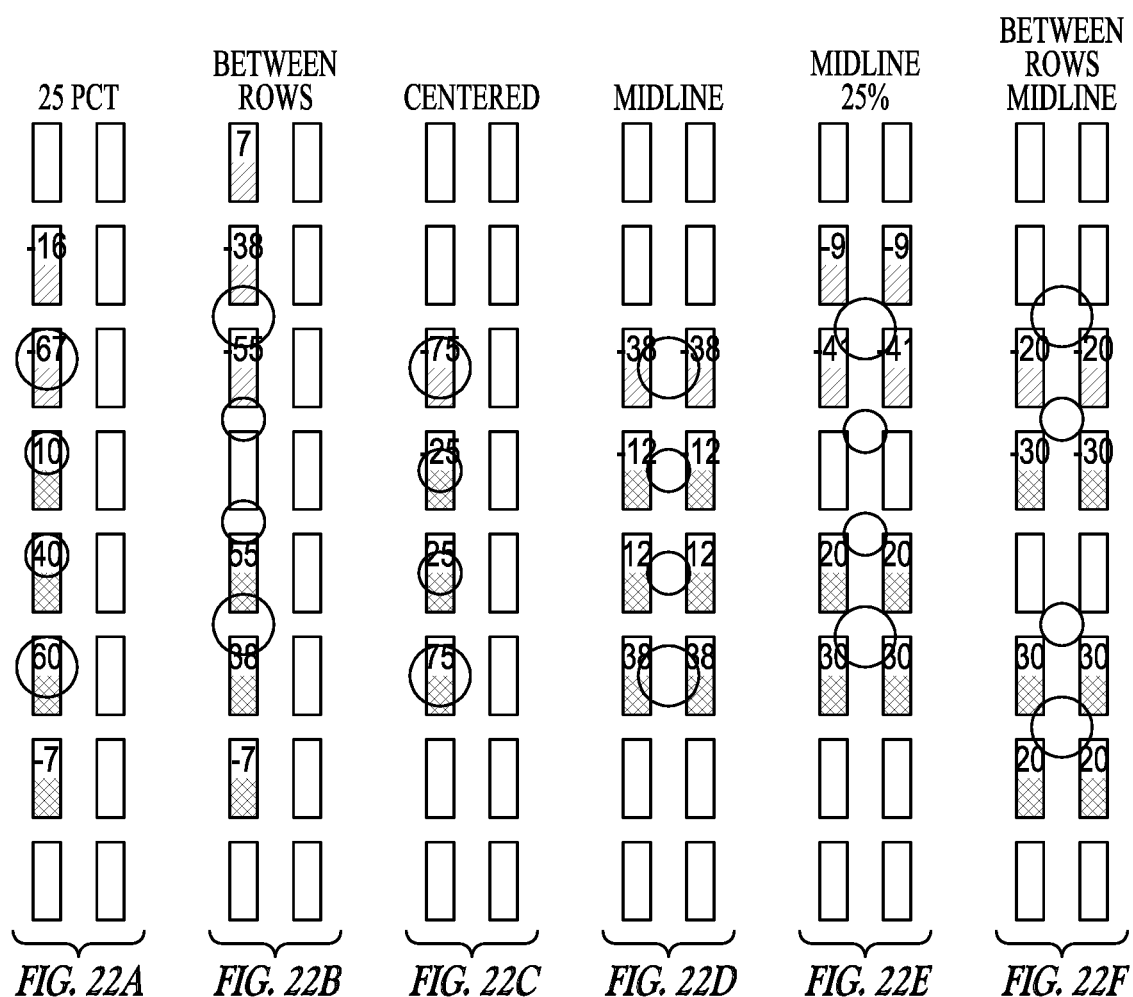

TOOL TO USE IMAGE FOR PROGRAMMING NEUROMODULATION

CLAIM OF PRIORITY

This application claims the benefit of priority under 35 U.S.C. § 119(e) of U.S. Provisional Patent Application Ser. No. 62/737,222, filed on Sep. 27, 2018, which is herein incorporated by reference in its entirety.

TECHNICAL FIELD

The present disclosure relates generally to medical devices, and more particularly, to systems, devices, and methods used in programming neuromodulation.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes. Some neural targets may be complex structures with different types of nerve fibers within a complex three dimensional environment. It is desirable to improve the precision of neural targeting and field shapes to for delivering neuromodulation to targeted regions within these complex structures.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example (e.g. Example 1) of subject matter (such as a system, a device, apparatus or machine) may be used with a medical imaging system and a programming system. The medical imaging system may be configured to display a medical image and the programming system may be configured to implement a program used in programming a neuromodulation device. The system may comprise a mobile device having at least one processor, a camera and a user interface including a display. The mobile device may be configured to acquire a displayed medical image from the medical imaging system where the displayed medical image includes a representation of anatomy and a representation of at least one lead and where the at least one lead includes electrodes, based on the acquired medical image determine location data indicative of the position of at least one of the electrodes relative to at least one of the anatomy or at least another one of the electrodes, and provide the location data for use by the program implemented by the programming system, wherein the programming system is configured to use the location data in programming the neuromodulation device.

In Example 2, the subject matter of Example 1 may optionally be configured such that the mobile device is configured to receive, using the user interface, user input annotating the acquired image to provide an annotated image.

In Example 3, the subject matter of any one or any combination of Examples 1-2 may optionally be configured such that the mobile device is configured to use the at least one processor to provide a reconstructed image for use by the programming system by reconstructing the representation of the at least one lead including electrodes on an anatomical template image.

In Example 4, the subject matter of any one or any combination of Examples 1-3 may optionally be configured such that the medical imaging system includes a fluoroscopy imaging system and the displayed image is a fluoroscopic image that includes a representation of at least one lead implanted proximate to a spine.

In Example 5, the subject matter of any one or any combination of Examples 1-4 may optionally be configured such that the mobile device includes a phone.

In Example 6, the subject matter of any one or any combination of Examples 1-5 may optionally be configured such that the acquired image includes an image from a picture taken by the camera of the mobile device.

In Example 7, the subject matter of any one or any combination of Examples 1-6 may optionally be configured such that the acquired image is a transitory image on the mobile device that is available for annotating the image and determining the location data but is not retrievably stored on the mobile device.

In Example 8, the subject matter of any one or any combination of Examples 1-7 may optionally be configured such that the mobile device is configured to directly communicate with the programming system to provide the location data for use by the program implemented by the programming system.

In Example 9, the subject matter of any one or any combination of Examples 1-8 may optionally be configured such that the mobile device is configured to provide the location data to the neuromodulation device, and the programming system is configured to receive the location data from the neuromodulation device.

In Example 10, the subject matter of any one or any combination of Examples 1-9 may optionally be configured such that the system is configured to move the location data from the mobile device to a cloud location and from the cloud location to the programming system.

In Example 11, the subject matter of any one or any combination of Examples 1-10 may optionally be configured such that the system is configured to display the annotated image with adjustable markers, and the adjustable markers are configured to be adjusted by the user to accommodate individual spinal anatomy.

In Example 12, the subject matter of any one or any combination of Examples 1-11 may optionally be configured such that the annotated image includes at least one marker to identify at least one of vertebral levels or laterality within the annotated image.

In Example 13, the subject matter of any one or any combination of Examples 1-12 may optionally be configured such that the mobile device is configured to use the annotated image to determine location data indicative of the positions of the electrodes and the anatomy.

In Example 14, the subject matter of any one or any combination of Examples 1-13 may optionally be configured such that the system includes a cloud device configured to use the annotated image to determine location data indicative of the positions of the electrodes and the anatomy.

In Example 15, the subject matter of any one or any combination of Examples 1-14 may optionally be configured such that the location data is usable by the programming system to determine energy contributions for the electrodes.

An example (e.g. Example 15) of subject matter (e.g. a method, a means for performing acts, or a machine-readable medium including instructions that, when performed by the machine, cause the machine to perform acts) may be performed using a medical imaging system and a programming system. The medical imaging system may be configured to display a medical image and the programming system may be configured to implement a program used in programming a neuromodulation device. The subject matter may include acquiring a displayed medical image from the medical imaging system, wherein the displayed medical image includes a representation of anatomy and a representation of at least one lead, wherein the at least one lead includes electrodes, receiving user input annotating the acquired image to provide an annotated image, based on the acquired medical image determine location data indicative of the position of at least one of the electrodes relative to at least one of the anatomy or at least another one of the electrodes, providing a reconstructed image for use by the programming system by reconstructing the representation of the at least one lead including electrodes on an anatomical template image, and providing the location data for use by the programming system to program the neuromodulation device.

In Example 17, the subject matter of Example 16 may optionally be configured such that the programming system is configured to use the location data to determine energy contributions for the electrodes.

In Example 18, the subject matter of any one or any combination of Examples 16-17 may optionally be configured such that the medical imaging system includes a fluoroscopy imaging system and the displayed image is a displayed fluoroscopic image, and the displayed image includes a representation of at least one lead implanted proximate to a spine.

In Example 19, the subject matter of any one or any combination of Examples 16-18 may optionally be configured such that acquiring the displayed image includes receiving a clipped image to capture a portion of the displayed fluoroscopic image.

In Example 20, the subject matter of any one or any combination of Examples 16-19 may optionally be configured such that acquiring the displayed image includes receiving an image from a picture taken of the displayed fluoroscopic image, wherein the picture is taken using a camera from a mobile device.

In Example 21, the subject matter of any one or any combination of Examples 16-20 may optionally be configured such that the acquired image is a transitory image on the mobile device that is available for annotating the image and determining the location data but is not retrievably stored on the mobile device.

In Example 22, the subject matter of any one or any combination of Examples 16-21 may optionally be configured such that receiving user input annotating the acquired image includes using the mobile device to receive user input to annotate the acquired image.

In Example 23, the subject matter of any one or any combination of Examples 16-22 may optionally be configured such that using the annotated image to determine location data includes using the mobile device to determine the location data from the annotated image or using the programming system to determine the location data from the annotated image.

In Example 24, the subject matter of any one or any combination of Examples 16-23 may optionally be configured such that using the annotated image to provide a reconstructed image includes using the mobile device to provide the reconstructed image from the annotated image or using the programming system to provide the reconstructed image from the annotated image.

In Example 25, the subject matter of any one or any combination of Examples 16-24 may optionally be configured such that a programming system has a camera, and the picture is taken using the camera of the programming system.

In Example 26, the subject matter of any one or any combination of Examples 16-25 may optionally be configured such that receiving user input annotating the acquired image includes at least one of: receiving user input annotating an orientation of the anatomy represented in the acquired image, or receiving user input annotating at least one label for a feature in the anatomy represented in the acquired image.

An example (e.g. Example 27) of subject matter (e.g. non-transitory computer-readable storage medium including instructions which when executed using at least one processor within a system cause the system to perform acts, a means for performing acts, or a method) may acquire a displayed medical image from a medical imaging system, wherein the displayed medical image includes a representation of anatomy and a representation of at least one lead, wherein the at least one lead includes electrodes, receive user input annotating the acquired image to provide an annotated image, based on the acquired medical image determine location data indicative of the position of at least one of the electrodes relative to at least one of the anatomy or at least another one of the electrodes, and provide the location data for use by at least one programming algorithm to program the neuromodulation device.

In Example 28, the subject matter of Example 27 may optionally be configured such that the programming system is configured to use the location data to determine energy contributions for the electrodes.

In Example 29, the subject matter of any one or any combination of Examples 27-28 may optionally be configured such that acquire a displayed medical image includes receive an image from a picture taken of the displayed image.

In Example 30, the subject matter of any one or any combination of Examples 27-29 may optionally be configured such that the system includes a phone with a camera, and the picture taken of the displayed image is taken by the phone.

In Example 31, the subject matter of any one or any combination of Examples 27-30 may optionally be configured such that the acquired image is a transitory image on the mobile device that is available for annotating the image and determining the location data but is not retrievably stored on the mobile device.

In Example 32, the subject matter of any one or any combination of Examples 27-31 may optionally be configured to cause the phone to receive user input annotating the acquired image to provide the annotated image.

In Example 33, the subject matter of any one or any combination of Examples 27-32 may optionally be configured such that the instructions, which when executed using the at least one processor, cause the phone to use the annotated image to provide the reconstructed image.

In Example 34, the subject matter of any one or any combination of Examples 27-33 may optionally be configured to cause the phone to use the annotated image to determine location data indicative of the positions of the electrodes and the anatomy.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 22A-22F generally illustrate the same target multipole with first and second target anodes and first and second target cathodes.

DETAILED DESCRIPTION

Figure 1:
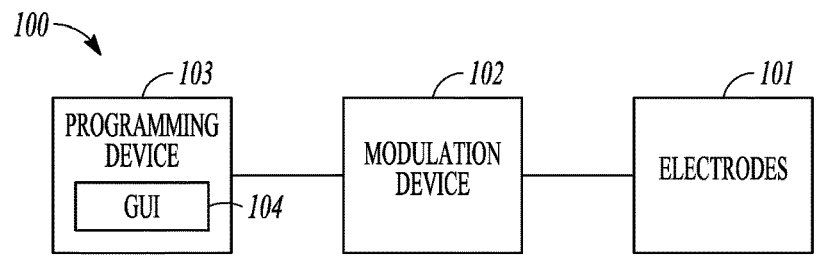
FIG. 1 illustrates, by way of example, an embodiment of a neuromodulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments described herein involve spinal cord modulation. The complex spinal cord structure resides in a complex three-dimensional environment. For example, the thickness of the cerebrospinal fluid (CSF), which is between the spinal cord and the epidural space, varies along the spine. Thus, the distance between the spinal cord and one or more neuromodulation leads within the epidural space likely varies. Furthermore, neither the leads nor the spinal cord form simple straight lines. The positions of implanted neuromodulation leads can also vary and are not perfectly parallel to the spinal cord. Additionally, the neuroanatomy of the spinal cord region can vary from patient-to-patient. It is desirable to accurately account for electrode positions to improve therapy programming.

A brief description of the physiology of the spinal cord is provided herein to assist the reader. A spinal cord includes white matter and gray matter. The gray matter includes cell bodies, synapse, dendrites, and axon terminals. White matter includes myelinated axons that connect gray matter areas. A typical transverse section of the spinal cord includes a central "butterfly" shaped central area of gray matter substantially surrounded by an ellipse-shaped outer area of white matter. The white matter of the dorsal column (DC) includes mostly large myelinated axons that form afferent fibers that run in an axial direction. The dorsal portions of the "butterfly" shaped central area of gray matter are referred to as dorsal horns (DH). In contrast to the DC fibers that run in an axial direction, DH fibers can be oriented in many directions, including perpendicular to the longitudinal axis of the spinal cord. Examples of spinal nerves include a dorsal root (DR), dorsal root ganglion and ventral root. The dorsal root mostly carries sensory signals into the spinal cord, and the ventral root functions as an efferent motor root. The dorsal and ventral roots join to form mixed spinal nerves.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been conventionally targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example. However, the patient does not sense the delivery of the modulation field (e.g. paresthesia) during a sub-perception therapy. Sub-perception therapy may modulate the spinal cord using a relatively high frequency modulation (e.g. about 1000 Hz or above). The high frequency modulation may include 1200 Hz or above, and may include 1500 Hz or above. Some embodiments herein selectively modulate DH tissue over DC tissue. Some embodiments selectively stimulate DR tissue and/or dorsal root ganglion over DC tissue to provide sub-perception therapy. Such selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. The selected modulation may be delivered with fixed or variable pulse widths.

FIG. 1 illustrates, by way of example, an embodiment of a neuromodulation system. The illustrated system 100 includes electrodes 101, a modulation device 102, and a programming system such as a programming device 103. The programming system may include multiple devices. The electrodes 101 are configured to be placed on or near one or more neural targets in a patient. For example, the electrodes 101 may be on one or more leads implanted within the subdural space of the spinal cord. The modulation device 102 is configured to be electrically connected to electrodes 101 and deliver modulation energy, such as in the form of electrical pulses, to the one or more neural targets though electrodes 101. The delivery of the modulation energy is controlled using a plurality of modulation parameters. The modulation parameters may specify the electrical waveform (e.g. pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 103 provides the user with accessibility to the user-programmable parameters. In various embodiments, the programming device 103 is configured to be communicatively coupled to modulation device via a wired or wireless link. In various embodiments, the programming device 103 includes a graphical user interface (GUI) 104 that allows the user to set and/or adjust values of the user-programmable modulation parameters.

Figure 2:
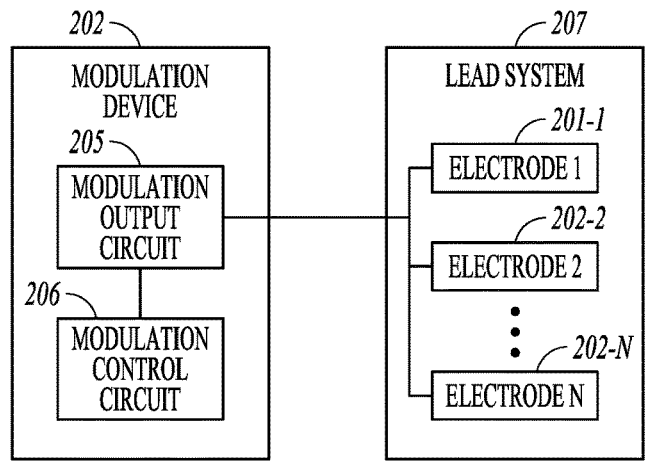
FIG. 2 illustrates an embodiment of a modulation device, such as may be implemented in the neuromodulation system of FIG. 1.

FIG. 2 illustrates an embodiment of a modulation device 202, such as may be implemented in the neuromodulation system 100 of FIG. 1. The illustrated embodiment of the modulation device 202 includes a modulation output circuit 205 and a modulation control circuit 206. Those of ordinary skill in the art will understand that the neuromodulation system 100 may include additional components such as sensing circuitry for patient monitoring and/or feedback control of the therapy, telemetry circuitry and power. The modulation output circuit 205 produces and delivers the modulation energy. Neuromodulation pulses are provided herein as an example. However, the present subject matter is not limited to pulses, but may include other electrical waveforms (e.g. waveforms with different waveform shapes, and waveforms with various pulse patterns). The modulation control circuit 206 controls the delivery of the neuromodulation pulses or other waveforms using the plurality of neuromodulation parameters. The lead system 207 includes one or more leads each configured to be electrically connected to modulation device 202 and a plurality of electrodes 201-1 to 201-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 205 and tissue of the patient, where $N \geq 2$. The neuromodulation pulses are each delivered from the modulation output circuit 205 through a set of electrodes selected from the electrodes 201-1 to 201-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes a paddle lead.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical waveforms (e.g. pulses) presents a huge selection of modulation parameter sets to the clinician or patient. For example, if the neuromodulation system to be programmed has sixteen electrodes, millions of modulation parameter sets may be available for programming into the neuromodulation system. Furthermore, for example, SCS systems may have thirty-two electrodes which exponentially increases the number of modulation parameters sets available for programming. To facilitate such selection, the clinician generally programs the modulation parameter sets through a computerized programming system to allow the optimum modulation parameters to be determined based on patient feedback or other means and to subsequently program the desired modulation parameter sets.

Figure 3:
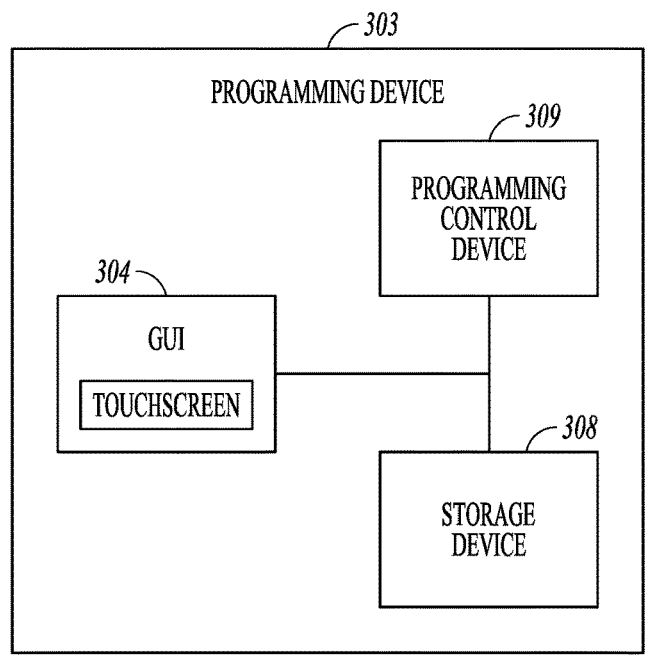
FIG. 3 illustrates an embodiment of a programming system such as a programming device, which may be implemented as the programming device in the neuromodulation system of FIG. 2.

FIG. 3 illustrates an embodiment of a programming system such as a programming device 303, which may be implemented as the programming device 103 in the neuromodulation system of FIG. 1. The programming device 303 includes a storage device 308, a programming control circuit 309, and a GUI 304. The programming control circuit 309 generates the plurality of modulation parameters that controls the delivery of the neuromodulation pulses according to the pattern of the neuromodulation pulses. In various embodiments, the GUI 304 includes any type of presentation device, such as interactive or non-interactive screens, and any type of user input devices that allow the user to program the modulation parameters, such as touchscreen, keyboard, keypad, touchpad, trackball, joystick, and mouse. The storage device 308 may store, among other things, modulation parameters to be programmed into the modulation device. The programming device 303 may transmit the plurality of modulation parameters to the modulation device. In some embodiments, the programming device 303 may transmit power to the modulation device. The programming control circuit 309 may generate the plurality of modulation parameters. In various embodiments, the programming control circuit 309 may check values of the plurality of modulation parameters against safety rules to limit these values within constraints of the safety rules.

In various embodiments, circuits of neuromodulation, including various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
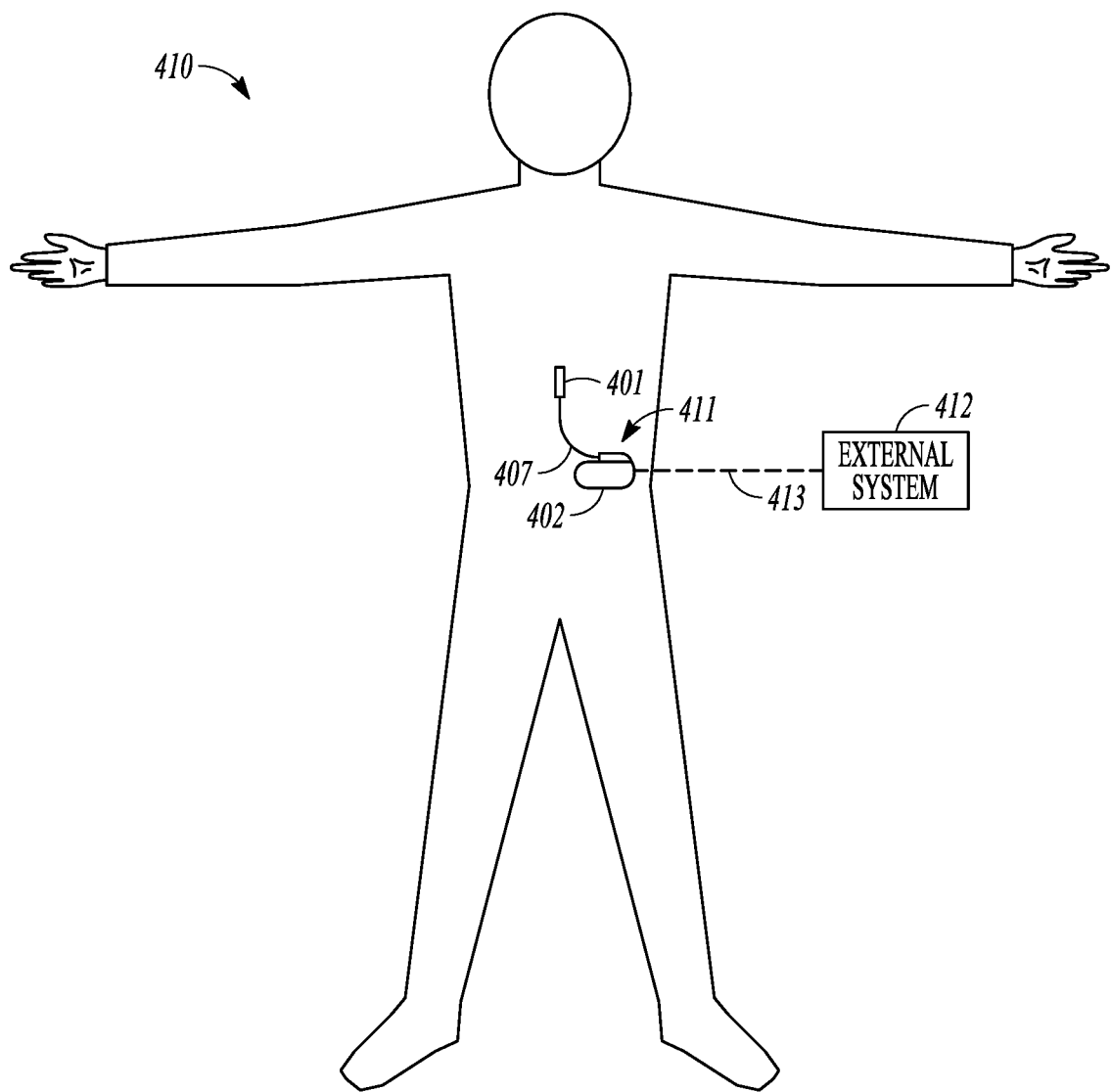
FIG. 4 illustrates, by way of example, an implantable neuromodulation system and portions of an environment in which system may be used.

FIG. 4 illustrates, by way of example, an implantable neuromodulation system and portions of an environment in which system may be used. The system is illustrated for implantation near the spinal cord. The illustrated system 410 includes an implantable system 411, an external system 412, and a telemetry link 413 providing for wireless communication between implantable system 411 and external system 412. The system 410 is illustrated as being implanted in the patient's body. The implantable system 411 includes an implantable neuromodulation device (also referred to as an implantable pulse generator, or IPG) 402, a lead system 407, and electrodes 401. The lead system 407 includes one or more leads each configured to be electrically connected to the modulation device 402 and a plurality of electrodes 401 distributed in the one or more leads. In various embodiments, the external system 412 includes one or more external (non-implantable) devices each allowing a user (e.g. a clinician or other caregiver and/or the patient) to communicate with the implantable system 411. In some embodiments, the external system 412 includes a programming device intended for a clinician or other caregiver to initialize and adjust settings for the implantable system 411 and a remote control device intended for use by the patient. For example, the remote control device may allow the patient to turn a therapy on and off and/or adjust certain patient-programmable parameters of the plurality of modulation parameters.

The neuromodulation lead(s) of the lead system 407 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 402 may be implanted in a surgically-made pocket either in the abdomen or above the buttocks, or may be implanted in other locations of the patient's body. The lead extension(s) may be used to facilitate the implantation of the implantable modulation device 402 away from the exit point of the neuromodulation lead(s).

Figure 5:
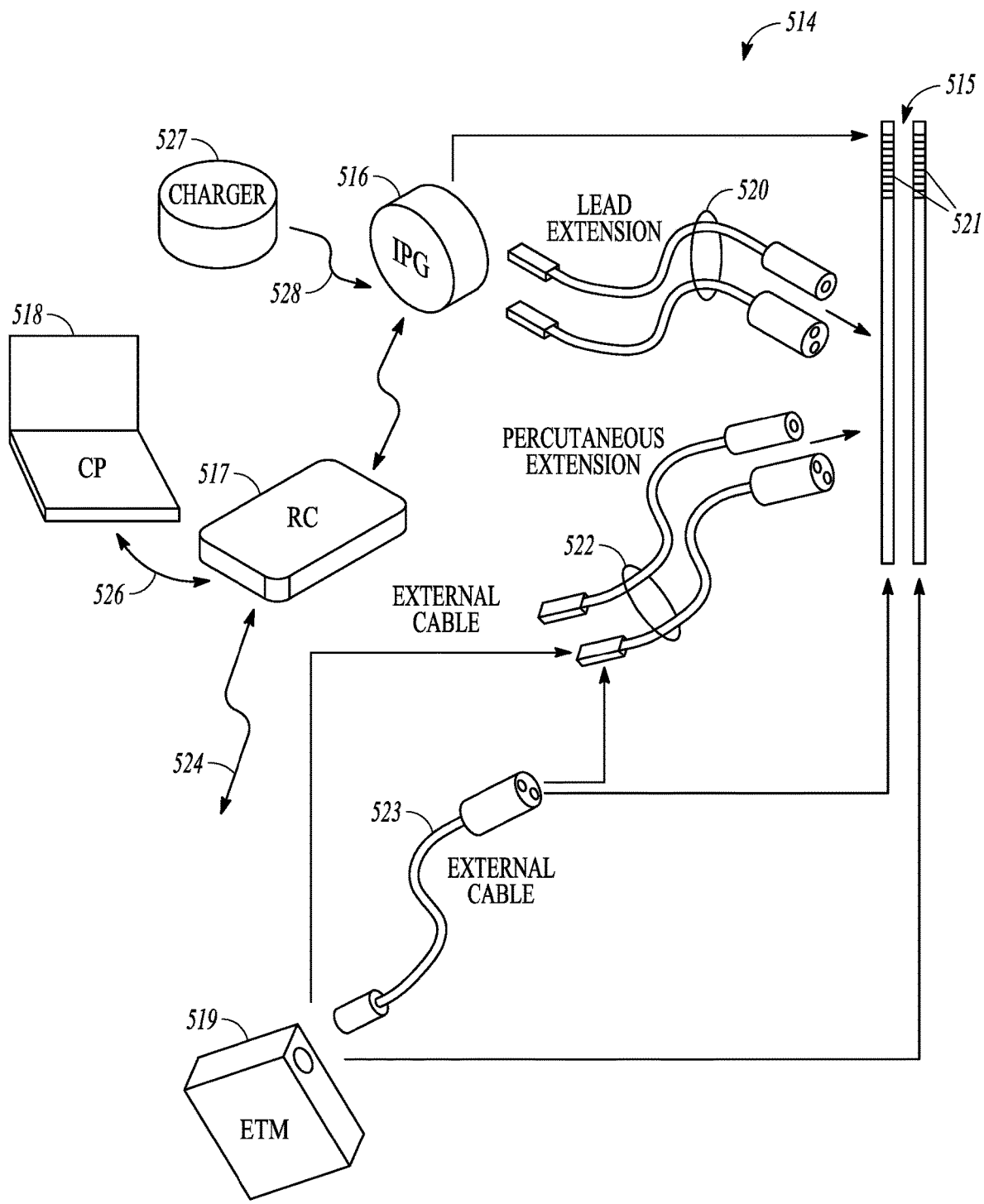
FIG. 5 illustrates, by way of example, an embodiment of a SCS system.

FIG. 5 illustrates, by way of example, an embodiment of a SCS system, which also may be referred to as a Spinal Cord Modulation (SCM) system. The SCS system 514 may generally include a plurality (illustrated as two) of implantable neuromodulation leads 515, an electrical waveform generator 516 such as an Implantable Pulse Generator (IPG), an external remote controller RC 517, a clinician's programmer (CP) 518, and an external trial modulator (ETM) 519. IPGs are used herein as an example of the electrical waveform generator. However, it is expressly noted that the waveform generator may be configured to deliver repeating patterns of pulses, irregular patterns of pulses where pulses have differing amplitudes, pulse widths, pulse intervals, and bursts with differing number of pulses. It is also expressly noted that the waveform generator may be configured to deliver electrical waveforms other than pulses. The waveform generator 516 may be physically connected via one or more percutaneous lead extensions 520 to the neuromodulation leads 515, which carry a plurality of electrodes 521. As illustrated, the neuromodulation leads 515 may be percutaneous leads with the electrodes arranged in-line along the neuromodulation leads. Any suitable number of neuromodulation leads can be provided, including only one. A surgical paddle lead can be used in place of one or more of the percutaneous leads. In some embodiments, the waveform generator 516 may include pulse generation circuitry that delivers electrical modulation energy in the form of a pulsed electrical waveform (i.e., a temporal series of electrical pulses) to the electrodes in accordance with a set of modulation parameters.

The ETM 519 may also be physically connected via the percutaneous lead extensions 522 and external cable 523 to the neuromodulation leads 515. The ETM 519 may have similar waveform generation circuitry as the waveform generator 516 to deliver electrical modulation energy to the electrodes accordance with a set of modulation parameters. The ETM 519 is a non-implantable device that is used on a trial basis after the neuromodulation leads 515 have been implanted and prior to implantation of the waveform generator 516, to test the responsiveness of the modulation that is to be provided. Functions described herein with respect to the waveform generator 516 can likewise be performed with respect to the ETM 519.

The RC 517 may be used to telemetrically control the ETM 519 via a bi-directional RF communications link 524. The RC 517 may be used to telemetrically control the waveform generator 516 via a bi-directional RF communications link 525. Such control allows the waveform generator 516 to be turned on or off and to be programmed with different modulation parameter sets. The waveform generator 516 may also be operated to modify the programmed modulation parameters to actively control the characteristics of the electrical modulation energy output by the waveform generator 516. A clinician may use the CP 518 to program modulation parameters into the waveform generator 516 and ETM 519 in the operating room and in follow-up sessions.

The CP 518 may indirectly communicate with the waveform generator 516 or ETM 519, through the RC 517, via an IR communications link 526 or other link. The CP 518 may directly communicate with the waveform generator 516 or ETM 519 via an RF communications link or other link (not shown). The modulation parameters provided by the CP 518 may also be used to program the RC 517, so that the modulation parameters can be subsequently modified by operation of the RC 517 in a stand-alone mode (i.e., without the assistance of the CP 518). Various devices may function as the CP 518. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 518. Alternatively, such programming methodologies can be performed using firmware or hardware. In any event, the CP 518 may actively control the characteristics of the electrical modulation generated by the waveform generator 516 to allow the desired parameters to be determined based on patient feedback or other feedback and for subsequently programming the waveform generator 516 with the desired modulation parameters. To allow the user to perform these functions, the CP 518 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant waveform generator, implant waveform generator and lead(s), replace waveform generator, replace waveform generator and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 527 may be a portable device used to transcutaneously charge the waveform generator via a wireless link such as an inductive link 528. Once the waveform generator has been programmed, and its power source has been charged by the external charger or otherwise replenished, the waveform generator may function as programmed without the RC or CP being present.

Figure 6:
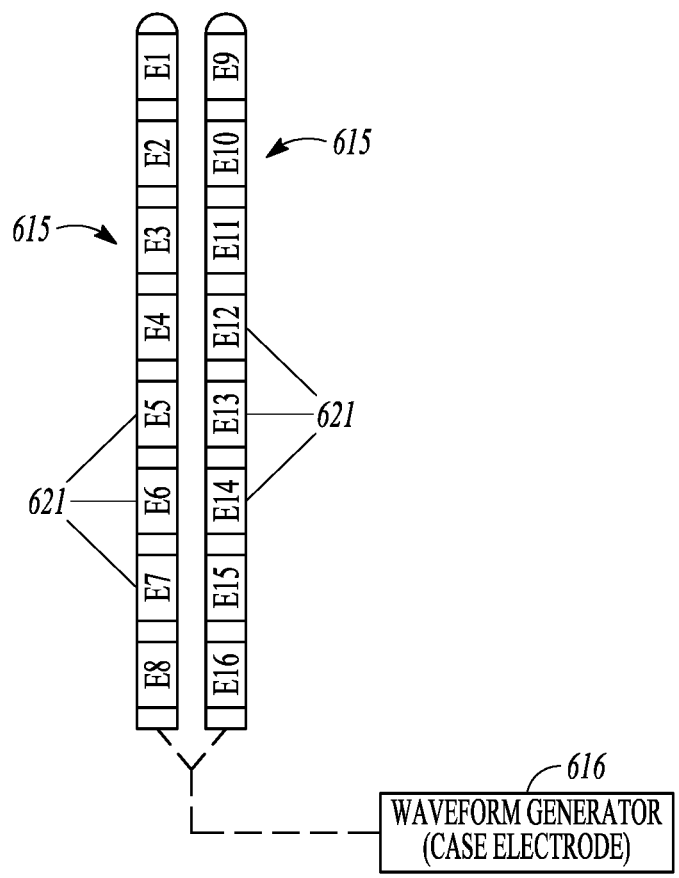
FIG. 6 illustrates, by way of example, some features of the neuromodulation leads and a waveform generator.

FIG. 6 illustrates, by way of example, some features of the neuromodulation leads 615 and a waveform generator 616. The waveform generator 616 may be an implantable device or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable waveform generator may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The waveform generator may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by the waveform generator. Electrical modulation energy is provided to the electrodes in accordance with a set of modulation parameters programmed into the pulse generator. By way of example but not limitation, the electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the case of the waveform generator. The system may be capable of transmitting modulation energy to the tissue in a monopolar or multipolar (e.g., bipolar, tripolar, etc.) fashion. Monopolar modulation occurs when a selected one of the lead electrodes is activated along with the case of the waveform generator, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The waveform generator may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The waveform generator may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices. Calibration techniques are used to determine the proper current fractionalization. With the current fractionalized to a plurality of electrodes on the electrical modulation lead, the resulting field can be calculated by superimposing the fields generated by the current delivered to each electrode.

Figure 7:
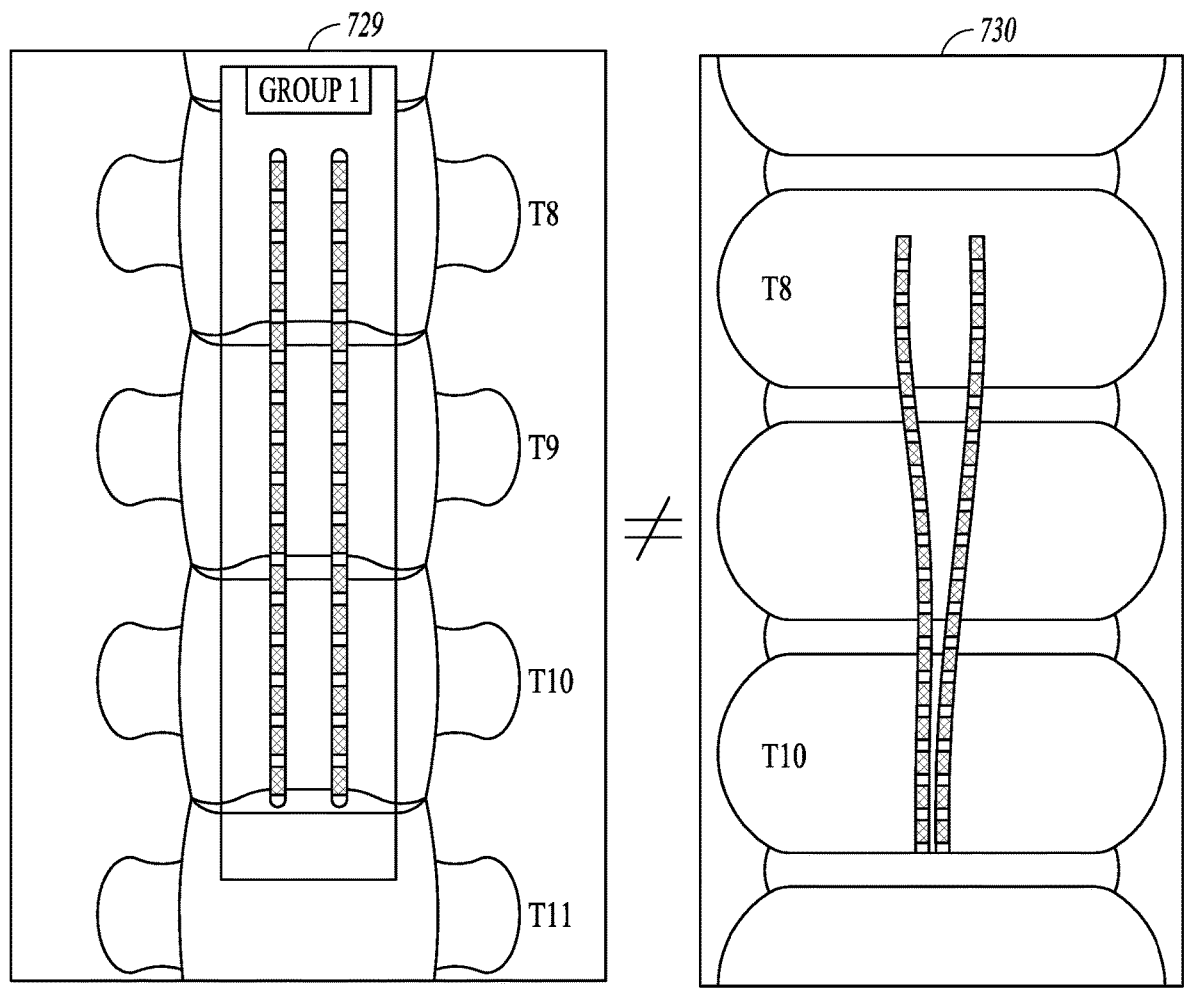
FIG. 7 illustrates, by way of example, some differences between a representation of leads within conventional user interface for a programming system and a representation of leads within a fluoroscopic image.

Embodiments of the present subject matter relate to systems, devices, and methods used in programming neuromodulation. FIG. 7 illustrates, by way of example, some differences between a representation of leads within conventional user interface for a programming system and a representation of leads within a fluoroscopic image. Current user interfaces, such as generally illustrated at 729, which are used to input information into programming systems assume leads are parallel. Thus, a simplified representation of parallel lead(s) may be included on an anatomical template (e.g. spinal levels T8-T10). However, in the real world, the leads are rarely parallel but rather may look similar to the fluoroscopic image illustrated at 730. Therefore, conventional user interfaces do not provide the real lead location information found in medical images such as fluoroscopic images, computed tomography (CT) images or magnetic resonance imaging (MRI) images. Thus, coordinates provided by conventional user interfaces to the programming systems do not accurately portray the real lead location. Additionally, the anatomical template in conventional user interfaces ignore patient-specific anatomical variations (e.g. differences in spinal levels) and anatomical locations (e.g. dorsal horn (DH) and dorsal column (DC) locations). Thus, it is not possible to develop reliable programming systems, even if improvements in lead detection are developed, because the way in which images are collected has not standardized in the field. For example, medical images such as fluoroscopic images commonly miss key information such as the laterality of the spine (what is right, what is left), and the vertebral levels that are contained in the image (e.g. identification of T9-10). The images may be flipped such that a later viewer will not know which sides represent the left and right sides of the patient. Also, if the image is zoomed in, then it may no longer include representations of anatomical landmarks such that the viewer may not be able to determine the vertebral level within the image. Also, as the images of the spine can vary, some embodiments provide a stretchable label (e.g. stretchable ruler) or individual markers to annotate the vertebral levels. The markers may be deformable to accommodate individual anatomical variations, vertebral levels, laterality, lead type, and the like. The user may be presented with predefined labeling that the user can drop onto the image to annotate it. Often, the user is able to annotate 2-3 vertebral levels within the image. However, the present subject matter is not limited to a particular number of vertebral levels. The system may be configured to enable a user to annotate lead(s) or electrode contact(s) or location information for the electrode contact(s).

Various embodiments of the present subject matter are able to present precise electrode contact position information to programming systems which may include anatomically-guided field algorithms. By way of example, a picture may be taken to capture at least a portion of a fluoroscopic image, the captured image may be annotated. Image processing may be performed to detect leads within the image (either before or after annotation) and determine coordinates, which may then be transferred to the ETM or IPG (see 519 and 516 in FIG. 5) such as via Bluetooth or other wireless or wired communication means. A realistic fluoroscopic representation may be projected onto a template in the CP (see 518 in FIG. 5). SCS programming is improved because of the realistic anatomical information provided to the CP. In some embodiments, the contact positions (e.g. precisely-determined coordinates from the fluoroscopic image) may be fed into the anatomically-guided field algorithms.

Figure 8A:
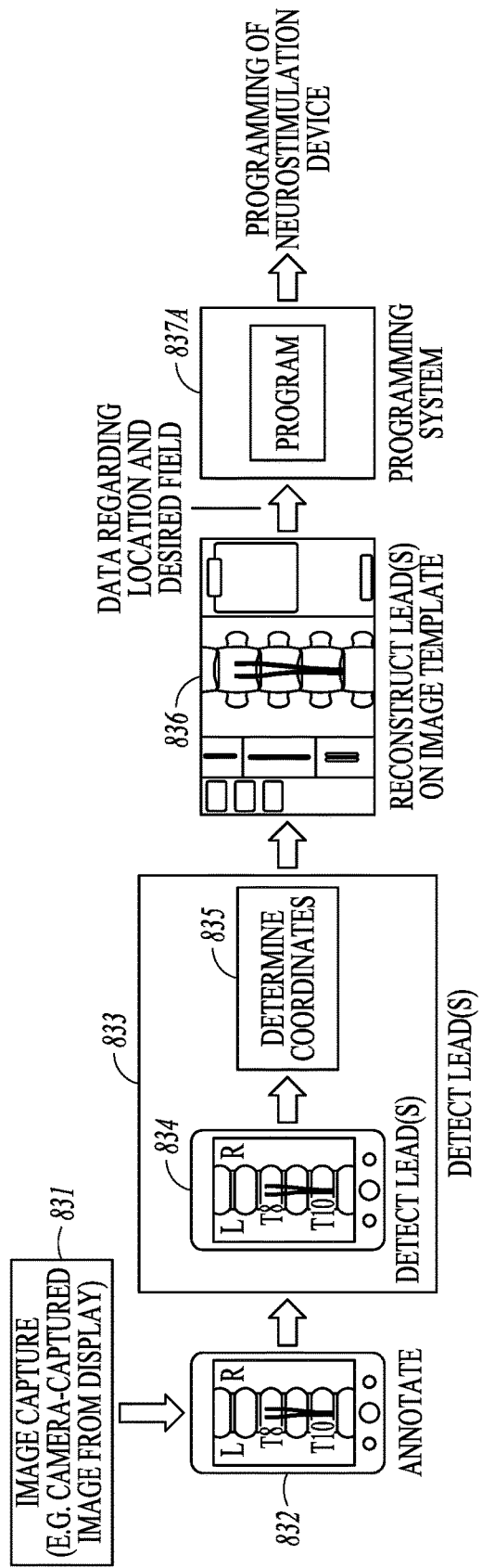
FIGS. 8A-8B illustrate, by way of example, an embodiment of a tool to use a medical image for neuromodulation programming.
Figure 8B:
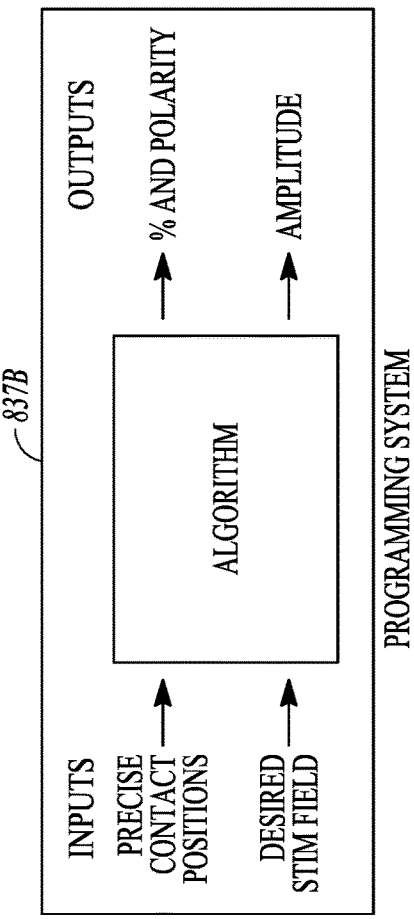

FIGS. 8A-8B illustrate, by way of example, an embodiment of a tool to use a medical image for neuromodulation programming. At 831 a displayed medical image is captured. For example, the medical image may be displayed during a procedure within an operating room. The captured image may be a portion of a medical image such as a fluoroscopic image. The image may be captured by a camera when the medical image is displayed on the medical imaging system. A camera in a mobile device, such as a phone or tablet, may be used to capture the image. The programmer may have a camera that may be used to capture the image when displayed on the medical imaging system. In some embodiments, the imaging system may have graphical controls to clip or snip a portion of the image. At 832 the image may be annotated. For example, when the image is captured by a mobile device such as a phone, the user interface (e.g. touch screen) of the mobile device may be used to annotate the image. The system is configured to display the annotated image with adjustable markers, and the adjustable markers are configured to be adjusted by the user to accommodate individual spinal anatomy. The annotated image includes at least one marker to identify at least one of vertebral levels (e.g. T8, T9, T10) or laterality (left or L and right or R) within the annotated image. At 833 image processing is performed. The image processing may detect the lead(s) and anatomical landmarks within the captured image as illustrated at 844 and may determine coordinates of the lead(s) and anatomical landmark(s) for use in identifying actual positions of the lead(s) and anatomical landmark(s) or the relative position of the lead(s) with respect to both each other and the anatomical landmark(s) as illustrated at 835. The image processing may be performed on the captured image or on the annotated image. At 836 lead(s) may be reconstructed on an image template, which may be used in user interface(s) that are configured for use to input information into the programming system. Such user interfaces may allow the user to also select a type of lead or the port of the neuromodulation device to which the lead is connected. The user interface is able to provide data regarding location(s) and a desired field(s) to the programming system (e.g. 837A in FIG. 8A or 837B in FIG. 8B). The programming system 837A or 837B may implement a program that is configured to use at least some of the data in programming the neuromodulation device. For example, the program may assist the clinician in selecting the appropriate stimulation configuration to achieve the desired field. Some embodiments of the programming system 837B may implement an algorithm, as generally illustrated in FIG. 8B, which is configured to receive inputs such as the precise electrode contact positions and the desired stimulation field, and determine the active electrode and the energy contributions provided by the active electrodes as well as the intensity of the stimulation. The intensity of the stimulation is illustrated as amplitude but other stimulation parameters such as pulse width, frequency, burst frequency, burst duration, and the like may be used to adjust the intensity. The programming system may use this information output by the algorithm to determine the appropriate neuromodulation parameter set to program into the neuromodulation device. It is noted that the illustrated functions may be implemented in other orders. For example, a portion or all of the image processing may be performed before or during the annotation function.

Figure 9:
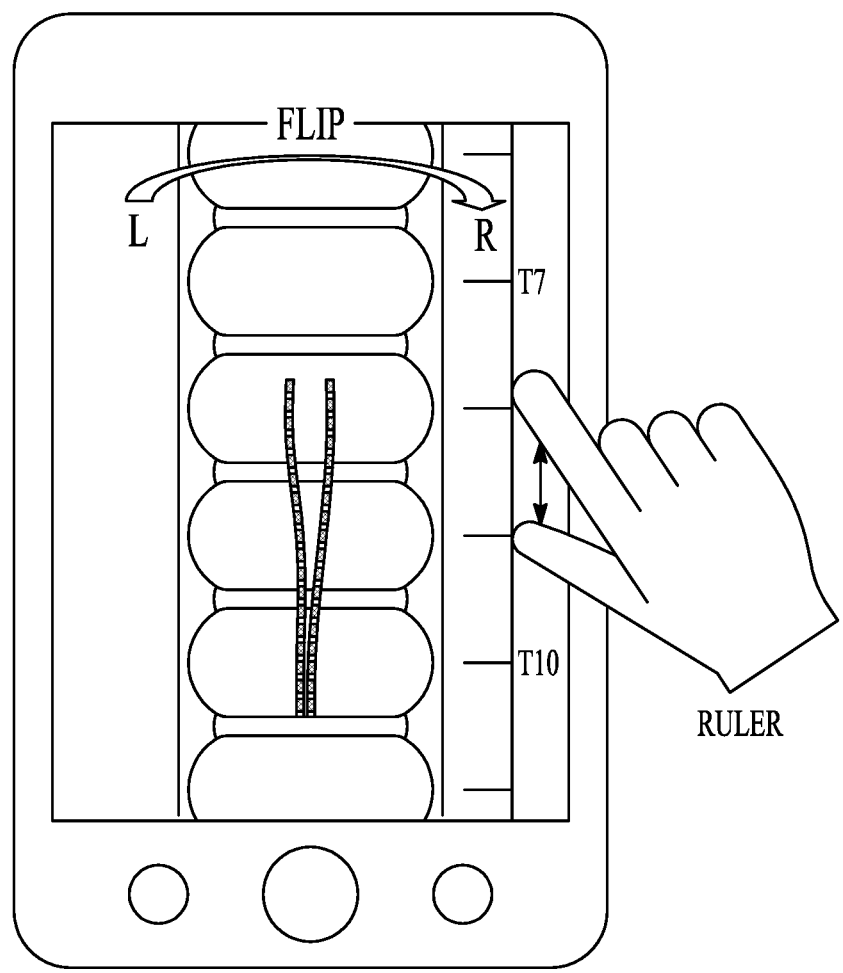
FIG. 9 illustrates, by way of example, some functionality for an embodiment of an annotation tool, such as may be implemented within the tool illustrated in FIGS. 8A-8B.

FIG. 9 illustrates, by way of example, some functionality for an embodiment of an annotation tool, such as may be implemented within the tool illustrated in FIGS. 8A-8B. For example the annotation tool may be implemented on a mobile device such as by an app on a phone or tablet, which may have been used to capture the image. However, the annotation tool may be implemented on other devices that have access to the image. As illustrated, the system is configured to display the annotated image with adjustable markers where the adjustable markers are configured to be adjusted by the user to accommodate individual spinal anatomy. The annotated image includes at least one marker to identify at least one of vertebral levels or laterality within the annotated image. More particularly, the illustrated embodiment includes a stretchable ruler with vertebrae markers. The illustrated embodiment also include interchangeable right and left markers. The app may also be capable of identifying a lead port to the neuromodulation device, a lead type, image processing algorithms that may be used to automatically detect leads and extract coordinates of contacts, and communicate with other devices within a programming system. For example, location data may be transferred via a communication protocol (e.g. Bluetooth) to an ETM or an IPG which were previously illustrated in FIG. 5.

Figure 10:
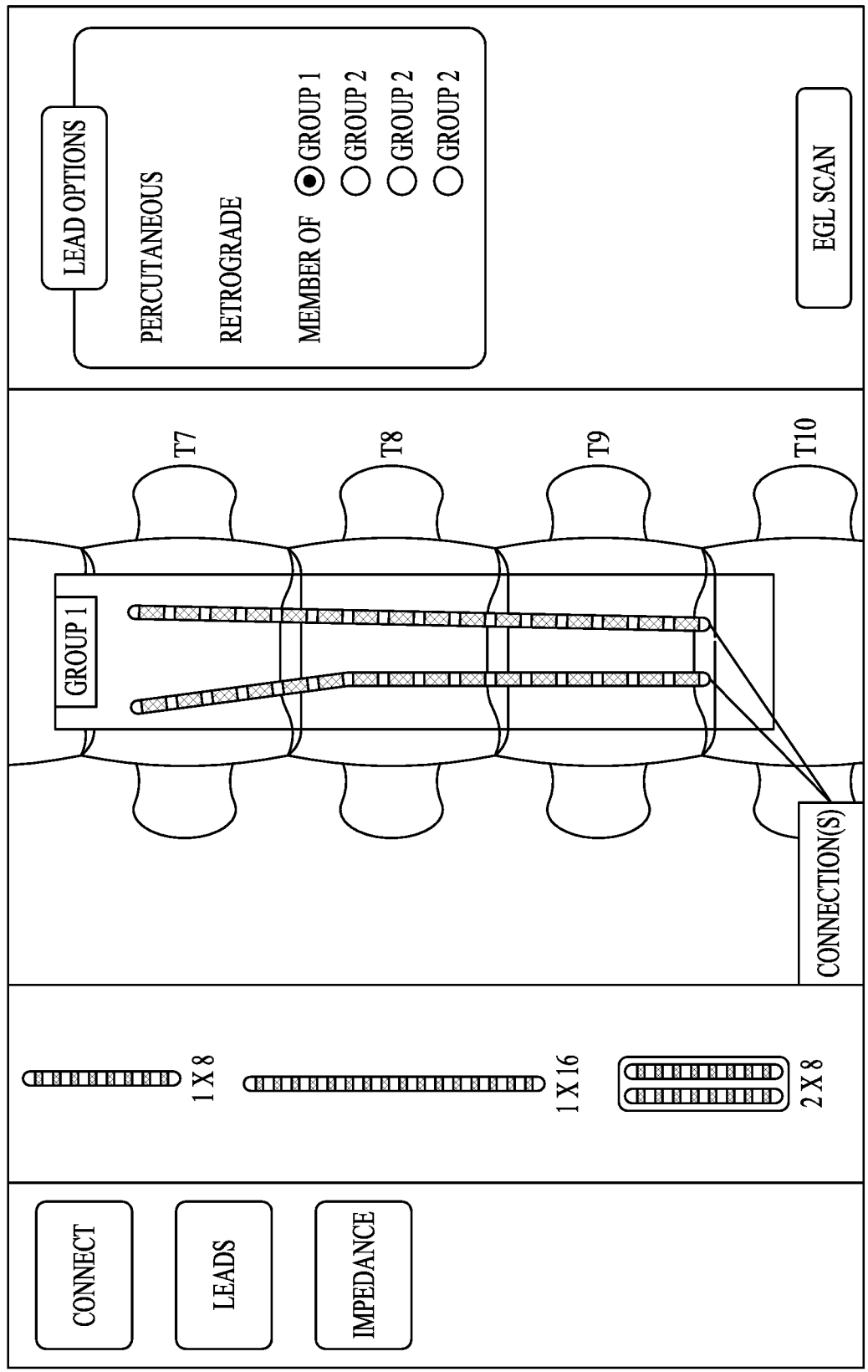
FIG. 10 illustrates, by way of example, an embodiment of a user interface configured for use to input information into the programming system.

FIG. 10 illustrates, by way of example, an embodiment of a user interface configured for use to input information into the programming system, such as was illustrated at 836 in FIG. 8A. The illustrated user interface includes a template of the spine with labeled vertebral levels with representations of the lead(s) accurately positioned over the template. Such user interfaces may allow the user to also select a type of lead (illustrated as "1×8", "1×16", "2×8") or the port of the neuromodulation device to which the lead is connected, illustrated as "connections", and other information that may be useful for the programming of the neuromodulation device with a stimulation configuration.

Figure 11:
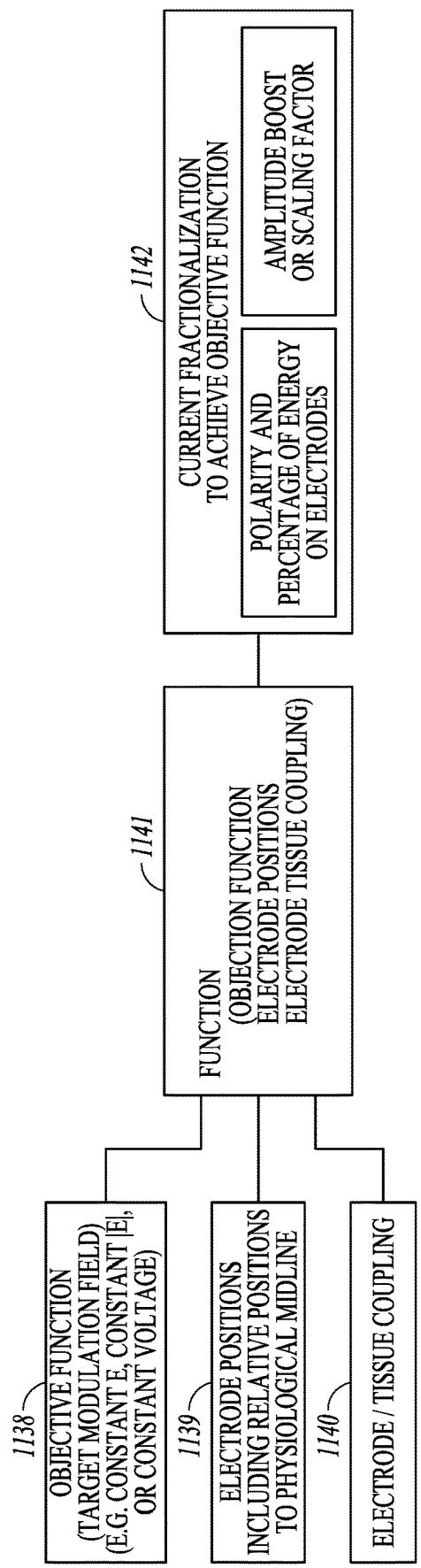
FIG. 11 illustrates, by way of example, an embodiment for determining fractionalization to achieve an objective function.

FIG. 11 illustrates, by way of example, an embodiment for determining fractionalization (e.g. percent and polarity of active electrodes as illustrated in FIG. 8B) to achieve an objective function. An objective function refers to a function with desirable characteristics for modulating the targeted tissue. The objective function may also be referred to as an objective target function. An objective function 1138 for a broad and uniform modulation field is identified for a given volume of tissue. Examples of an objective function includes a constant E (electric field), a constant |E| (electric field magnitude), and a constant voltage. The lead and electrode configuration 1139, including relative positions to a physiological midline, are also identified, as well as electrode tissue coupling 1140. A function 1141 is performed that is dependent on the objective function, the electrode positions, and the electrode tissue coupling. The result of the function is the fractionalization of modulation energy (e.g. current) 1142 for each electrode to achieve the objective function. The fractionalization of modulation energy may be expressed, for each electrode, as a polarity (e.g. cathodic or anodic) and percentage of the total cathodic energy or total anodic energy delivered to the plurality of electrodes on the lead at a given time. Furthermore, an amplitude boost or scaling factor may be applied to the fractionalization values.

Figure 12:
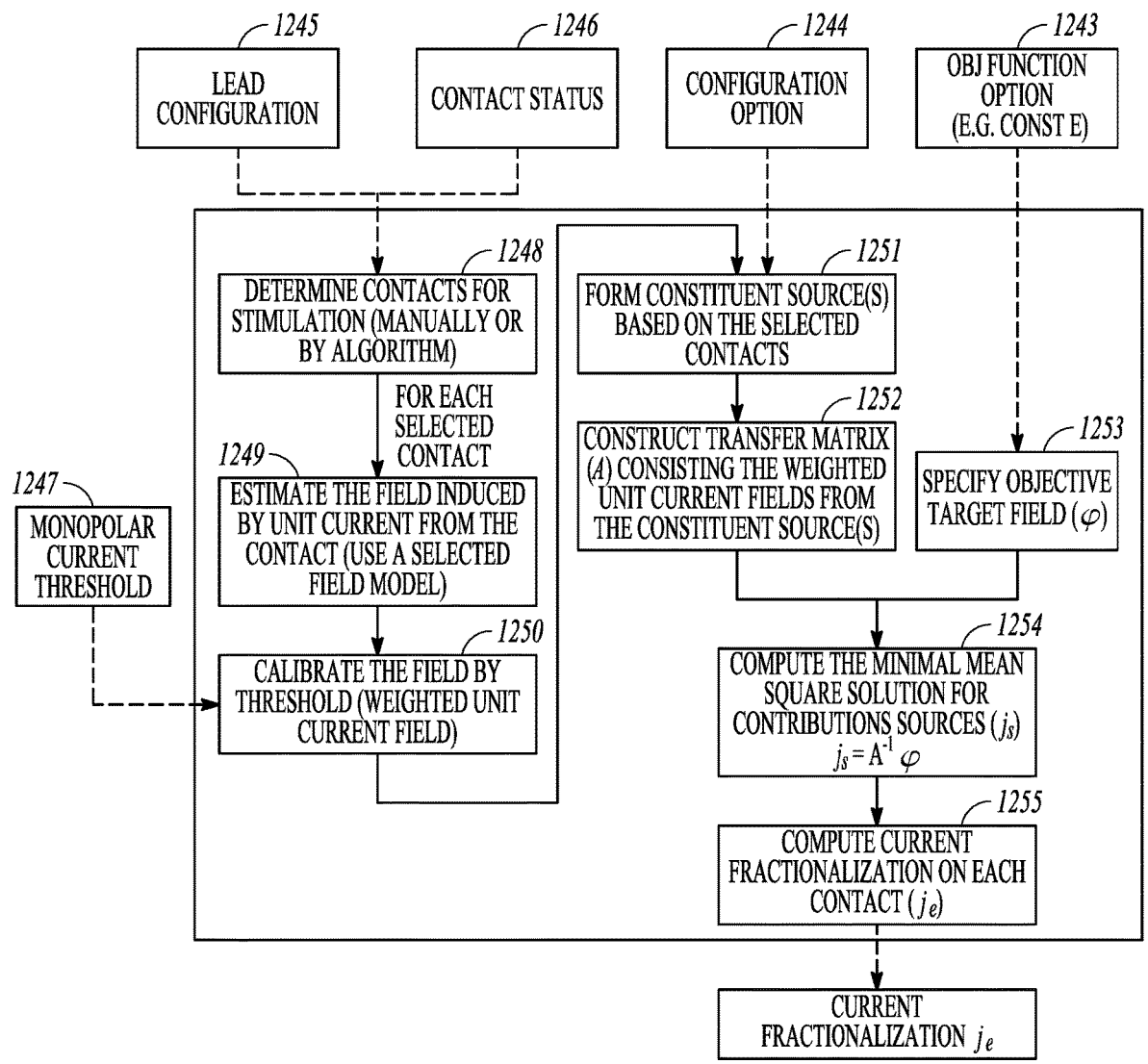
FIG. 12 illustrates, by way of example, an embodiment for determining fractionalization to achieve an objective function with more detail.

FIG. 12 illustrates, by way of example, an embodiment for determining fractionalization to achieve an objective function with more detail. An objective target function 1243 (e.g. constant E) is provided as an input to a process. Other inputs to the process include a configuration option 1244, a lead configuration 1245 and electrode contact status 1246, and a threshold 1247 such as a current threshold like a monopolar current threshold. The lead configuration 1245 and contact status 1246 identify an electrode arrangement, identifying a position of each electrode to determine the field. The overall field is a superimposed field from each electrode. The configuration option 1244 refers to monopolar (same polarity for all activated electrodes) and multipolar options (combined anode and cathodes in field). The threshold is used to compensate for electrode/tissue coupling differences.

The contacts for stimulation may be determined automatically or manually 1248 from the lead configuration and contact status. A selected field model may be used to estimate the field induced by unit current from the contact 1249. The field may be calibrated using the threshold 1250. For example, the unit current field may be weighted. Constituent forces may be formed based on the selected contacts 1251, and a transfer matrix 1252 may be constructed for use to compute the minimal mean square solution 1254 using contributions from the constituent sources and using a specified target field 1253. The solution may be used to compute the current fractionalization on each contact 1255.

Figure 13:
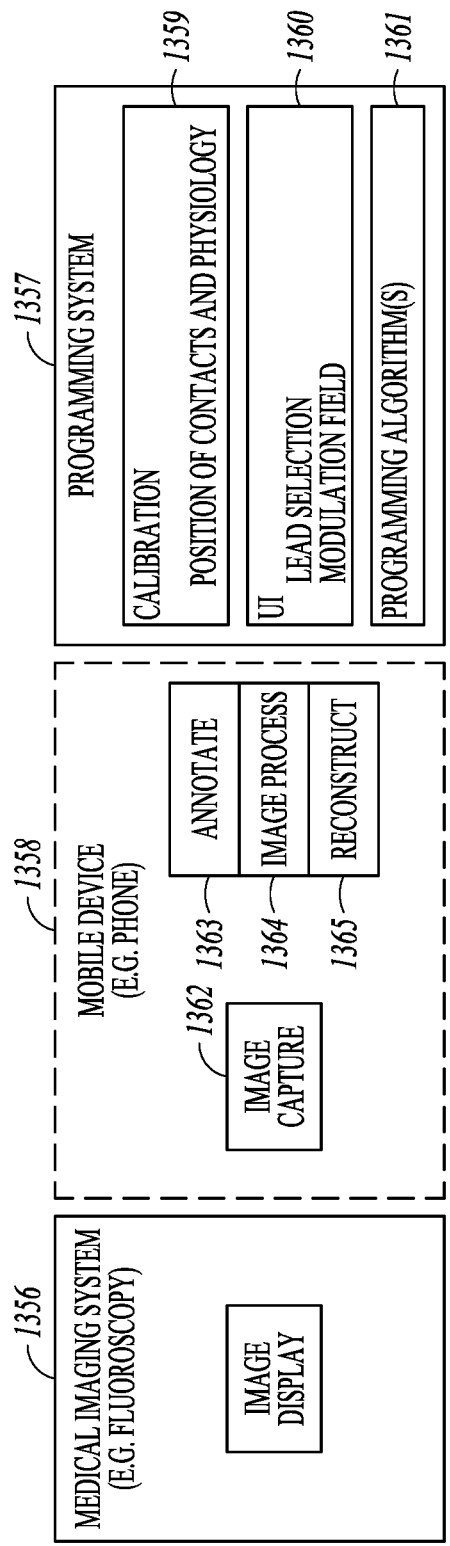
FIG. 13 illustrates a medical imaging system, a programming system for programming a neuromodulator such as a spinal cord stimulation (SCS) system, and bridging functions provided by the tool illustrated in FIGS. 8A-8B to provide information to the programming system based on a displayed image (e.g. fluoroscopic image) in the medical imaging system.

FIG. 13 illustrates a medical imaging system 1356, a programming system 1357 for programming a neuromodulator such as a spinal cord stimulation (SCS) system, and bridging functions 1358 such as may be provided by the tool illustrated in FIGS. 8A-8B to provide information to the programming system based on a displayed image (e.g. fluoroscopic image) in the medical imaging system. The bridging functions 1358 provide an informational bridge between the medical imaging system 1356 and the programming system 1357. The programming system 1357 may include a single device such as a CP, or may include two or more devices such as, by way of example and not limitation, two or more of an RC, CP, and cloud-based system which may work together to program the neuromodulator. The programming system 1357 may include a calibration feature 1359 that is configured to use the location information (e.g. coordinates) to determine the relative or actual positions of the electrode contacts and physiological features. The programming system 1357 may include a user interface 1360, such as the interface illustrated in FIG. 10 for example, that may be configured for use to select leads and modulation fields. The programming system 1357 may include anatomically-guided field algorithms 1361 for use to generate the stimulation configurations, including the energy contributions for individual electrode contacts to provide the shape and size of the modulation field.

The bridging functions 1358 determine information contained within the medical image and provide data based on the medical image information for use by the programming system 1357 to improve programming capabilities. The bridging functions 1358 may include an image capture function 1362, an annotation function 1363, an image processing function 1364 and an image reconstruction function 1364. These bridging functions 1358 may be performed using one device or may be distributed across two or more devices. The bridging functions 1358 may be implemented using device(s) that are separate from the medical imaging system 1356 and the programming system 1357 or some of the bridging functions 1358 may be implemented using at least one of the medical imaging system 1356 or the programming system.

Figure 14:
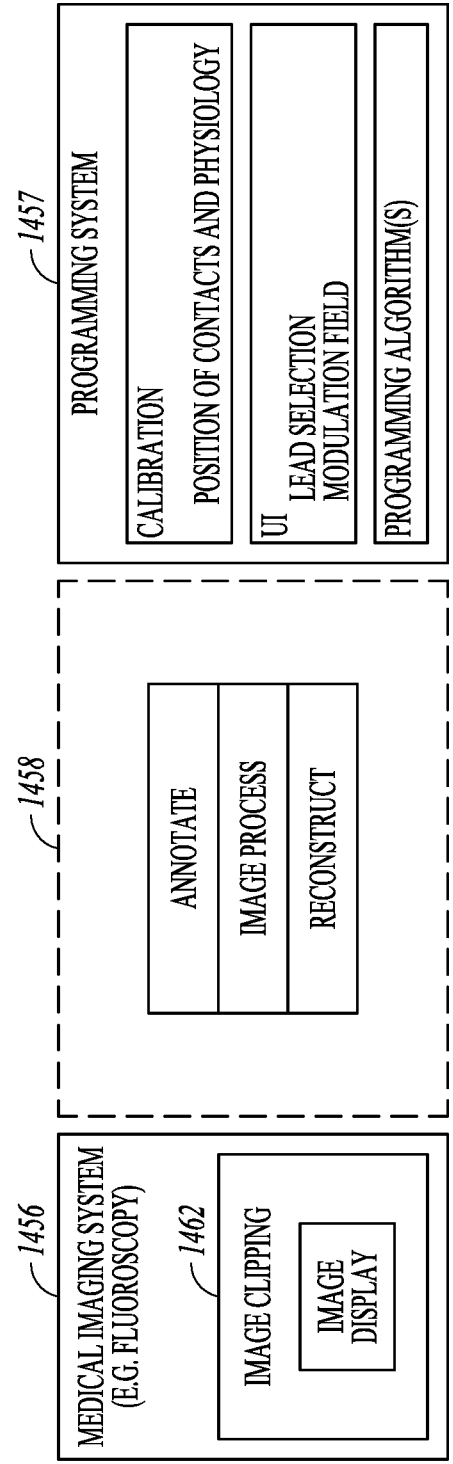
FIG. 14 illustrates an example of a system in which the image capture function is performed using the medical imaging system.

FIG. 14 illustrates an example of a system in which the image capture function 1462 is performed using the medical imaging system 1456. For example, the medical imaging system 1456 may have graphical editing tools, such as snipping/clipping/copy tools, allowing the user to select a portion of the displayed image such as may be done by dragging a cursor to create a selection window on the displayed image. The selected portion is a captured image. The image may then be shared with and used by other bridging functions 1458 to determine information contained within the medical image and provide data based on the medical image information to improve programming capabilities of the programming system 1457.

Figure 15:
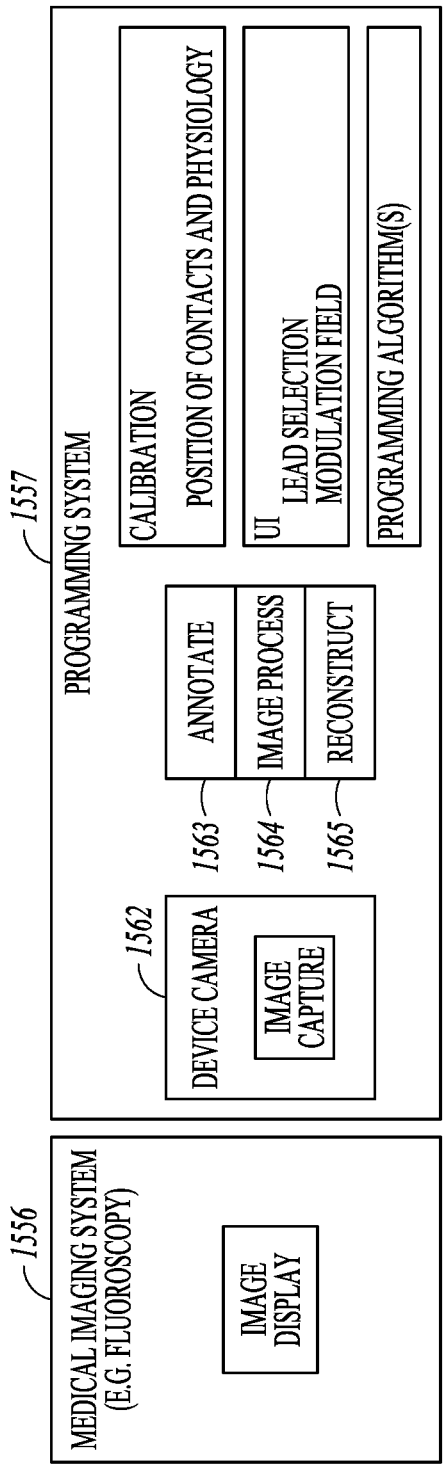
FIG. 15 illustrates an example of a system in which the programming system is configured to perform the bridging functions.

FIG. 15 illustrates an example of a system in which the programming system 1557 is configured to perform the bridging functions and the programming system 1557 based on a displayed image (e.g. fluoroscopic image) in the medical imaging system 1556. The bridging functions may be performed by one device or distributed over two or more devices within the programming system 1557. For example, a CP may include a device camera 1562 and an app or other program for providing image annotation 1563, image processing 1564 and image reconstruction 1565. Thus, a CP may use a camera to capture an image from the image display, and be configured to enable a user to annotate the image and perform image processing to determine coordinates, and be configured to perform image reconstruction to provide an accurate representation of electrode contact location with respect to anatomical features beneficial for programming a neuromodulation device.

Figure 16:
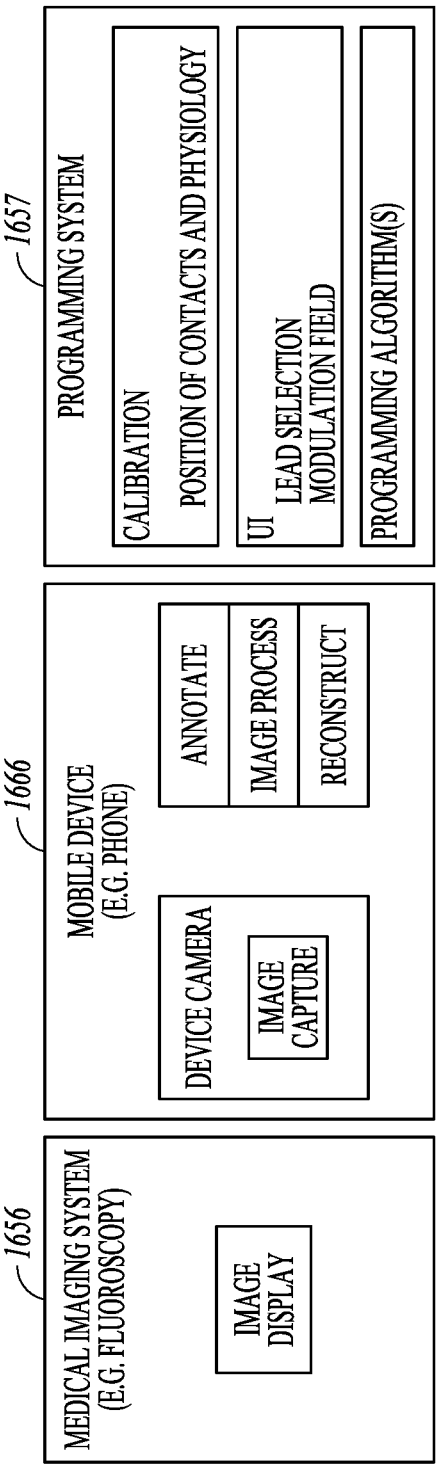
FIG. 16 illustrates an example of a system that includes a mobile device such as a phone programmed with an app or otherwise configured to perform the bridging functions between a displayed image (e.g. fluoroscopic image) in the medical imaging system and the programming system.

FIG. 16 illustrates an example of a system that includes a mobile device 1666 such as a phone programmed with an app or otherwise configured to perform the bridging functions between a displayed image (e.g. fluoroscopic image) in the medical imaging system 1656 and the programming system 1657. Thus, a phone may be may use a camera to capture an image from the image display, and be configured to enable a user to annotate the image and perform image processing to determine coordinates, and be configured to perform image reconstruction to provide an accurate representation of electrode contact location with respect to anatomical features beneficial for programming a neuromodulation device. The mobile device is not limited to phones, as it may include tablets, laptops, and other devices.

Figure 17:
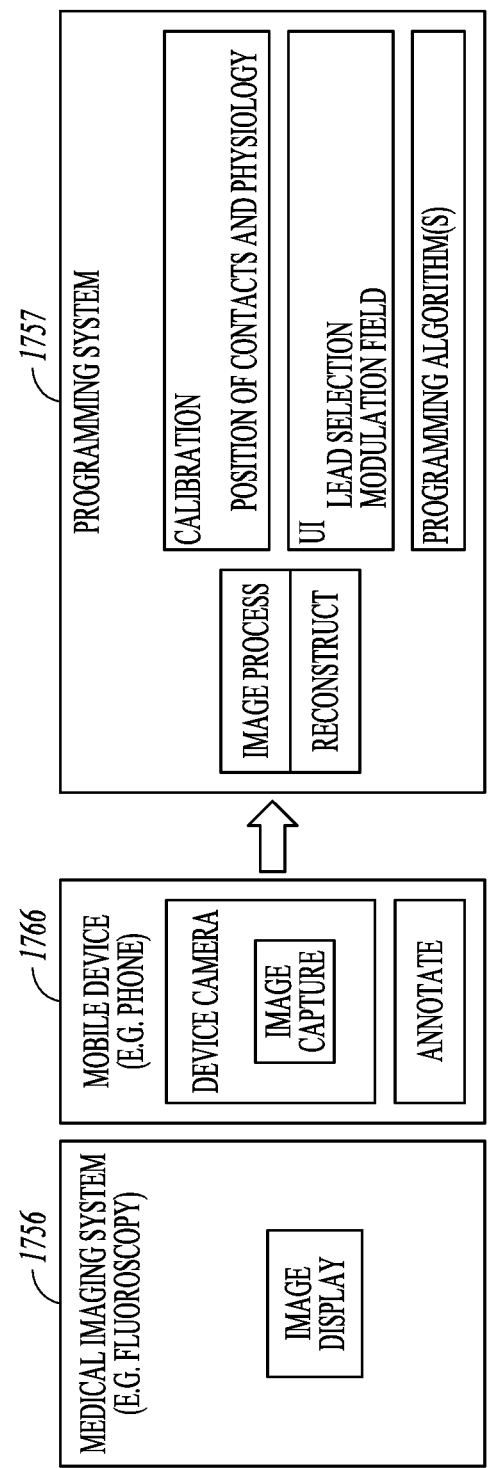
FIG. 17 illustrates an example of a system that includes a mobile device such as a phone or tablet programmed with an app or otherwise configured to perform a portion of the bridging functions between a displayed image (e.g. fluoroscopic image) in the medical imaging system and the programming system, and the programming system is configured to perform another portion of the bridging functions.

FIG. 17 illustrates an example of a system that includes a mobile device 1766 such as a phone or tablet programmed with an app or otherwise configured to perform a portion of the bridging functions between a displayed image (e.g. fluoroscopic image) in the medical imaging system 1756 and the programming system 1757, and the programming system 1757 is configured to perform another portion of the bridging functions. Thus, by way of example and not limitation, an app operating a phone may use the phone's camera to capture an image from the displayed image from the medical imaging system, and may be configured to enable a user to annotate the captured image using the phone touch screen interface. The programming system 1757 may be configured to perform image processing to determine coordinates, and be configured to perform image reconstruction to provide an accurate representation of electrode contact location with respect to anatomical features beneficial for programming a neuromodulation device.

The type of data that moves between the various components depend on the bridging functions that being performed by the components. The data may include data indicative of the captured image. The data may include data indicative of the annotated image. The data may include data indicative of the location of electrode contacts, location of lead(s), and location of anatomical feature(s). The location data may include coordinates to establish absolute or relative positions of the electrode contact(s) to the anatomical feature(s). Examples of anatomical features may include DC or DH fibers or a nerve root or ganglia at one or more targeted vertebral levels.

Some embodiments specifically exclude Personally Identifiable Information (PII) and Protected Health Information (PHI) from being retrievably stored or transferred to the programming system. Examples of PII include but are not limited to name, social security numbers, driver's license or other identification numbers, citizenship, gender, race, birth date and telephone numbers. For example, fluoroscopic images may include meta data which may identify the patient's name, hospital, and the like. Examples of PHI include but are not limited to lab test results, health histories, diagnosis, and the like. Various embodiments intentionally exclude PII/PHI information from the captured image taken from the fluoroscopic image. Various embodiments intentionally prevent PII/PHI information from being retrievably stored in the mobile device or other device within the system. The prevention of PII/PHI data from being retrievably stored may allow a temporary possession of the data in a transitory or ephemeral way. However, users are unable to access that data within the course of normal operations. For example, the mobile device app does not save an image beyond the current session, but will only save coordinates and an identifier that does not qualify as a PII or PHI data.

Figure 18:
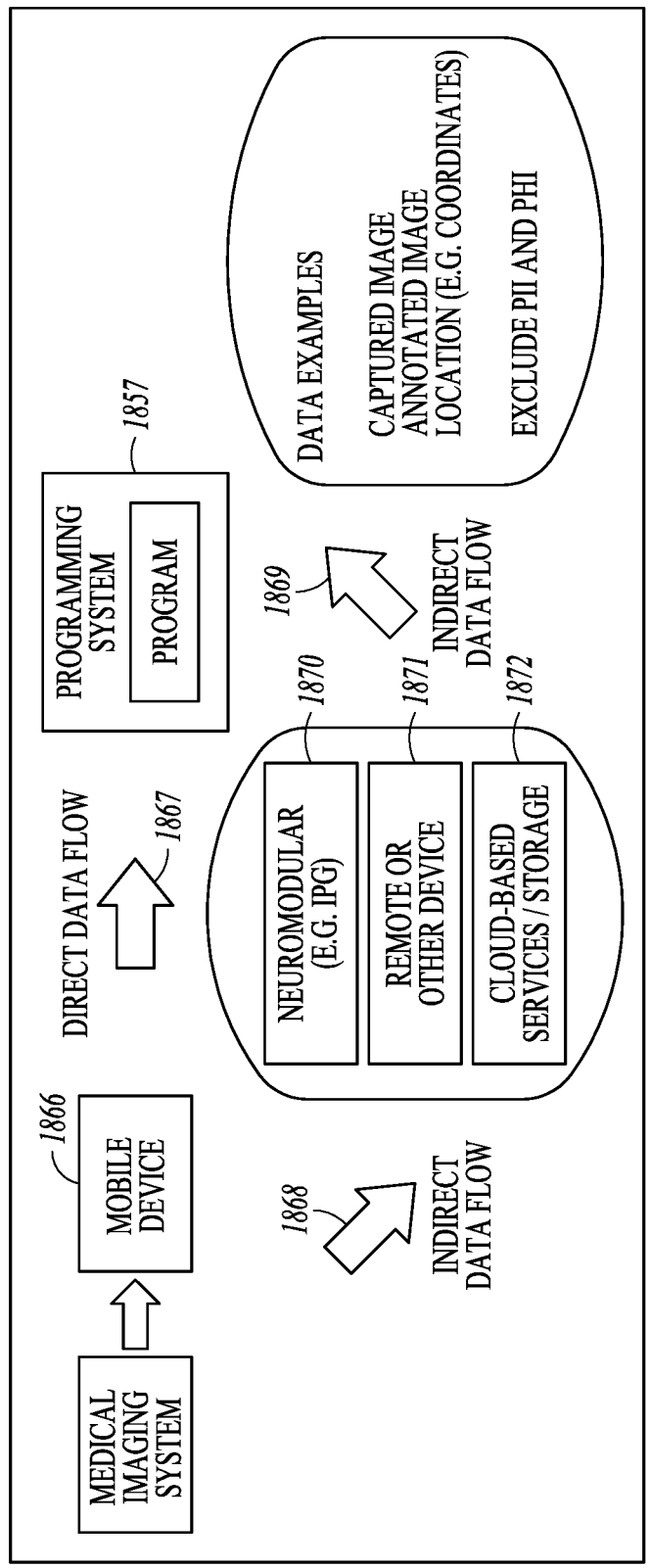
FIG. 18 illustrates examples of data flow that may occur within various system embodiments.

FIG. 18 illustrates examples of data flow that may occur within various system embodiments. For example, as illustrated at 1867, the mobile device 1866 may be configured to directly communicate with the programming system 1857 to provide the data (e.g. data indicative of location such as coordinates or image-related data from which location can be determined) for use by the program implemented by the programming system. Additionally or alternatively, as illustrated at 1868 and 1869, the data may be indirectly provided to the programming system 1857 through a neuromodulator such as the implantable pulse generator (IPG) 1870, or through a patient remote control or other device 1871, or through cloud-based service(s) and/or storage 1872. By way of example, embodiments that store the data in the neuromodulator (IPG or ETS) may assist with the deidentification of the data because it would like the data to the device and not the patient directly. The system may be designed to provide the data to the programming system using any one or any two or more of the illustrated ways. Thus, for example, the mobile device may be configured to provide the location data directly to the programming system and may also be configured to provide the location data to the neuromodulation device and the programming system is configured to receive the location data from the neuromodulation device. In some embodiments, the mobile device may provide the data (e.g. data indicative of location such as coordinates or image-related data from which location can be determined) to a cloud-based service(s)/storage, and the programming system can receive the data indicative of location such as coordinates or image-related data from which location can be determined from the cloud-based service(s)/storage. Some embodiments may use a cloud-based platform at a cloud location to provide the image processing and/or annotation and/or image reconstruction functions. The data indicative of location provided to the programming system (e.g. CP) may include data indicative of electrode-to-electrode distances and electrode-to anatomical feature distances.

Figures 19A, 19B:
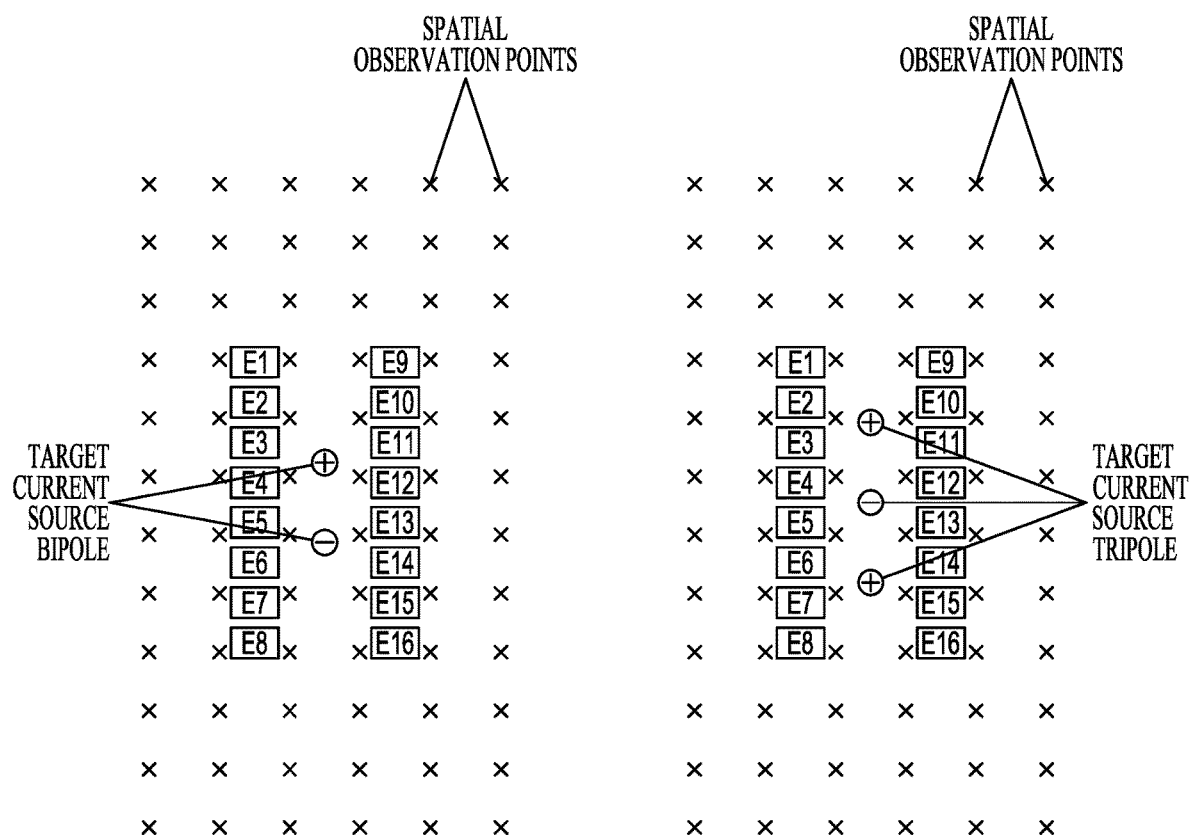
FIGS. 19A-B illustrate, by way of example, mapping a target electrical field to an electrode array.

The programming system (e.g. CP) may implement a program that is configured to use the location data indicative of positions of electrodes and the anatomy to program the neuromodulation device. With reference to FIGS. 19A-19B, the CP may implement programming algorithms to map a target electrical field to the electrode array by estimating the field potential values (or some other linear electrical parameter, such as an activating function, current density, etc.) of the target field at a plurality of spatial observation points. The CP may accomplish this by determining the desired locations of target current source poles relative to the electrode array, and modeling an electrical field generated by the target current source poles to determine desired field potential values at the spatial observation points (e.g., using analytical and/or numerical models).

Although target current source poles are one way to represent a "target electrical field", other representations of target fields may be used. The locations of the target current source poles may be determined in a manner that places the resulting electrical field over an identified region of the patient to be stimulated. The spatial observation points may be spaced in a manner that would, at the least, cover the entire tissue region to be stimulated and/or would not cover a tissue region that should not be stimulated. The locations of the target current source poles may be defined by the user, and may be displayed to the user along with the electrode locations, which as briefly discussed above, may be determined based on electrical measurements taken at the electrodes. The CP may select, or allow a user to select, a plurality of constituent current sources at the locations of the electrodes. The locations of the electrodes may be determined, at least in part, based on the displayed image within the medical imaging system. Additionally or alternatively, some embodiments may determine electrode locations based on measurements taken at the electrodes in response to sub-threshold electrical signals transmitted between the electrodes.

Once the constituent sources are selected, the CP may determine the relative strengths of the constituent current sources that, when combined, result in estimated electrical field potential values at the spatial observation points that best matches the desired field potential values at the spatial observation points. In particular, the CP may model the constituent current sources (e.g., using analytical and/or numerical models) and estimate the field potential values per unit current (V/mA) generated by each of the constituent current sources at the spatial observation points, and may generate an m×n transfer matrix (shown in FIG. 20) from the estimated field potential values per unit current, with m equaling the number of spatial observation points and n equaling the number of constituent sources. The relative strengths of the constituent current sources may be determined using an optimization function that includes the transfer matrix A and the desired field potential values.

The optimization function may be a least-squares (over-determined) function expressed as: $|\varphi - A\hat{j}|^2$, where $\varphi$ is an m-element vector of the desired field potential values, A is the transfer matrix, and $\hat{j}$ is an n-element vector of the strengths of the constituent current sources. The constituent current source strengths $\hat{j}$ may be solved such that the optimization function $|\varphi - A\hat{j}|^2$ is minimized. The square difference is minimized if $\varphi = A\hat{j}$. One approach for solving this problem may be to invert the transfer matrix A and pre-multiply, such that $A^{-1} = \varphi A^{-1} A\hat{j}$, which yields the solution $\hat{j} = A^{-1}\varphi$. Once the strengths of the constituent current sources are determined, the CP converts these strengths to current distributions on the electrodes in the form of a polarity and percentage.

Improving the precision of the location data for the electrodes and anatomical target(s) input into these algorithms enhance the effectiveness of the programmed stimulation configuration. Such improvements may be useful for delivering sub-perception modulation of the DH or DR tissue over DC tissue. However, some embodiments may be used to deliver other modulation therapies.

Neural tissue in the region of the spinal cord has different characteristics. For example, DC fibers (mostly myelinated axons) run in an axial direction, whereas DH (e.g. neuronal cell terminals, neuronal cell bodies, dendrites, and axons) fibers are oriented in many directions. The distance from typically-placed epidural SCS leads to DH fibers are different than the distance from these leads to DC fibers. Further, DH fibers and dorsal column fibers have different responses (e.g. activation functions) to electrical modulation. The strength of modulation (i.e., depolarizing or hyperpolarizing) of the DC fibers and neurons is described by the so-called "activation function" which is proportional to the second-order spatial derivative of the voltage along the longitudinal axis of the spine ($\partial 2V/\partial x2$). This is partially because the large myelinated axons in DC are primarily aligned longitudinally along the spine. On the other hand, the likelihood of generating action potentials in DH fibers and neurons is described by an activating function that is proportion to the first-order spatial derivative of the voltage along the spine ($\partial V/\partial x$), which is otherwise known as the electric field. Thus, the DH activating function is proportional to the first-order derivative of the voltage along the fiber axis, whereas the DC activating function is proportional to the second-order derivative of the voltage along the fiber axis. Accordingly, the distance from the electrical field locus affects the DH activating function ($\partial V/\partial x$) less than it affects the dorsal column activating function $\partial 2V/\partial x2$. The neuronal elements (e.g., neurons, dendrites, axons, cell bodies, and neuronal cell terminals) in the DH can be preferentially stimulated over the DC neuronal elements by minimizing the longitudinal gradient of an electrical field generated by a neuromodulation lead along the DC, thereby providing therapy in the form of pain relief without creating the sensation of paresthesia. DH fibers and DC fibers have different responses (activation functions) to electrical modulation.

Various embodiments for enhancing modulation field selectively modulate DH and/or DR tissue over DC tissue. Conventional SCS activates DC fiber axons, and the orthodromic propagation of action potentials induces perception of paresthesia in the brain and antidromic propagation of action potentials to fiber collaterals and terminals ending in DH evokes pain control mechanism in DH. Various embodiments shape the stimulation field to preferably stimulate fiber terminals ending in DH and/or DR to provide pain relief without inducing paresthesia. For example, uniformity in a first order gradient of voltage (i.e. uniformity in electric field) may be more efficient in stimulating DH fiber terminals and/or stimulating DR fibers. Uniformity across a larger field may eliminate the needs for searching optimal stimulation site and create broader coverage of pain. For example, the uniformity may extend between or among two or more electrodes within an arrangement of electrodes. In other examples, the uniformity may extend among three, four, five, six or more electrodes within an arrangement of electrodes to eliminate the needs for searching for an optimal simulation site and creating a broader therapeutic coverage. Thus, the uniformity extends over a substantial portion of the lead. Some embodiments are configured to determine a modulation parameter set to create a field shape to provide a broad and uniform modulation field to enhance modulation of targeted neural tissue (e.g. DH tissue or DR tissue). Some embodiments are configured to determine a modulation parameter set to create a field shape to reduce or minimize modulation of non-targeted tissue (e.g. DC tissue).

Various embodiments disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of DH neural tissue and to minimize the modulation of DC tissue. A benefit of MICC is that MICC accounts for various in electrode-tissue coupling efficiency and perception threshold at each individual contact. This capability of MICC along with precise location data determined from the captured image improves the ability to precisely apply a modulation field with a desirable shape to precisely target neuroanatomy For example the modulation field may be shaped to provide a constant electric field (E) at the DH tissue in a selected direction. The electric field (E) at the DH in any direction is the negative gradient (negative rate of change) of the scalar potential field (V) in that direction. Due to the linearity of field superposition, a transfer function can be formed to estimate the EDH(x,y,z) at selected direction induced by unit current from a single electrode located at (x0, y0, z0), the total E field is the linear combination of the E field induced by currents from each active electrode weighted by the current fractionalization. In an example, the modulation field may be a constant V field along the DC tissue. Due to the linearity of field superposition, a transfer function can be formed to estimate the VDC(x,y,z) at selected direction induced by unit current from a single electrode located at (x0, y0, z0), the total V field is the linear combination of the V field induced by currents from each active electrode weighted by the current fractionalization.

Various embodiments may design a field to maximize the linear progression of extracellular voltages in the rostral-caudal direction for subthreshold and suprathreshold activation of terminals oriented in the anterior posterior (AP) direction. Various embodiments of the present subject matter produce a linear field by stacking fractionalizations of target poles in a directional, progressive manner.

Figures 20, 21:
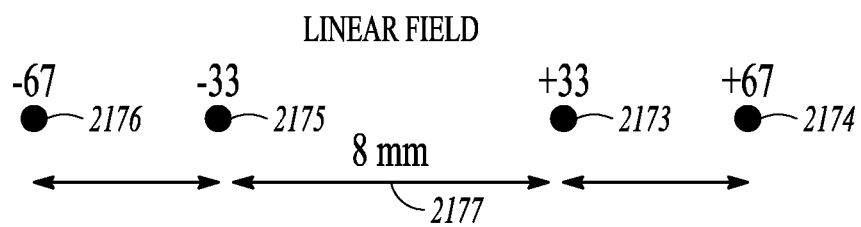
FIG. 20 illustrates an m×n transfer matrix used to determine the relative strengths of constituent current sources.
FIG. 21 illustrates an embodiment of a target multipole that includes fractionalized target anodes and fractionalized target cathodes designed to maximize the electric field in a region while minimizing the "activating function" (i.e. activation of dorsal columns, axons of passage) represented by the second difference of the extracellular potentials generated by a field.

As a particular example, FIG. 21 illustrates an embodiment of a target multipole that includes fractionalized target anodes and fractionalized target cathodes designed to maximize the electric field in a region while minimizing the "activating function" (i.e. activation of dorsal columns, axons of passage) represented by the second difference of the extracellular potentials generated by a field. The target multipole illustrated in FIG. 21 progressively stacks fractionalization of target poles. The illustrated target multipole may be referred to as a base field design, as it may serve as a base from which the field length, width and orientation may be adjusted, and as a base from which features such as flanking electrodes may be added. In the illustrated embodiment, the target multipole includes first and second target anodes where in the first target anode 2173 represents 33% of the total anodic current and the second target anode 2174 represents 67% of the total anodic current; and further includes first and second target cathodes where in the first target cathode 2175 represents 33% of the total cathodic current and the second target anode 2176 represents 67% of the total cathodic current. Other percentages may be used to progressively increase the percentage moving away from the center of the target multipole and/or to alter the length of the target field. Some embodiments may include more than two target anodes in which the percentage of anodic current progressively increases away from the center of the target multipole. Some embodiments may include more than two target cathodes in which the percentage of cathodic current progressively increases away from the center of the target multipole. Some embodiments may include one target anode (100%) and more than one target cathode. Some embodiments may include one target cathode (100%) and more than one target anode.

As a more particular example, FIGS. 22A-22F generally illustrate the same target multipole with first and second target anodes and first and second target cathodes. The second target anode is larger than the first target anode, and the second target cathode is larger than the first target cathode. The fractionalized current delivered to the underlying physical electrodes may be adjusted to precisely move the target multipole, by way of example and not limitation, to be centered laterally on the left column of electrodes with the target poles centered longitudinally at 25% from the electrode top (FIG. 22A), to be centered laterally on the left column of electrodes with the target poles centered longitudinally between rows in the left column of electrodes (FIG. 22B), to be centered laterally on the left column of electrodes with the target poles centered longitudinally on electrodes in the left column of electrodes (FIG. 22C), to be centered laterally on a midline between the columns and centered longitudinally with electrode rows (FIG. 22D), to be centered laterally on a midline between the columns with the target poles centered longitudinally at 25% from the electrode row top (FIG. 22E), and to be centered laterally on a midline between the columns with the target poles centered longitudinally between rows of electrodes (FIG. 22F).

Various embodiments disclosed herein may use a computer system, within which a set or sequence of instructions may be executed to cause the machine to perform methodologies discussed herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, the term "machine" shall also be taken to include any collection of machines that individually or jointly execute a set (or multiple sets) of instructions to perform any one or more of the methodologies discussed herein. One or more machines that are controlled by or operated by one or more processors (e.g., a computer) to individually or jointly execute instructions to perform any one or more of the methodologies discussed herein.

An example of a computer system includes at least one processor (e.g., a central processing unit (CPU), a graphics processing unit (GPU) or both, processor cores, compute nodes, etc.), a main memory and a static memory, which communicate with each other via a link (e.g., bus). The computer system may further include a video display unit, an alphanumeric input device (e.g., a keyboard), and a user interface (UI) navigation device (e.g., a mouse). In one embodiment, the video display unit, input device and UI navigation device are incorporated into a touch screen display. The computer system may additionally include a storage device (e.g., a drive unit), a signal generation device (e.g., a speaker), a network interface device, and one or more sensors (not shown), such as a global positioning system (GPS) sensor, compass, accelerometer, or other sensor. It will be understood that other forms of machines or apparatuses (such as IPG, RC, CP devices, and the like) that are capable of implementing the methodologies discussed in this disclosure may not incorporate or utilize every one of these components (such as a GPU, video display unit, keyboard, etc.). The storage device may include a machine-readable medium on which is stored one or more sets of data structures and instructions (e.g., software) embodying or utilized by methodologies or functions described herein. The instructions may also reside, completely or at least partially, within the main memory, static memory, and/or within the processor during execution thereof by the computer system, with the main memory, static memory, and the processor also constituting machine-readable media. While the machine-readable medium is illustrated in an example embodiment to be a single medium, the term "machine-readable medium" may include a single medium or multiple media (e.g., a centralized or distributed database, and/or associated caches and servers) that store the one or more instructions. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. The instructions may further be transmitted or received over a communications network using a transmission medium via the network interface device utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A method performed using a mobile device with a medical imaging system and a programming system, wherein the medical imaging system is configured to display a medical image and the programming system is configured to implement a program used in programming a neuromodulation device, the method comprising using the mobile device to provide information to the programming system based on a displayed medical image in the medical imaging system, including using the mobile device to:
    acquire the displayed medical image from the medical imaging system, wherein the displayed medical image includes a representation of anatomy and a representation of at least one lead, wherein the at least one lead includes electrodes, wherein the acquiring the displayed image includes taking a picture of the displayed medical image using a camera from the mobile device;
    receive user input annotating the acquired image to provide annotations in an annotated image;
    determine location data based on the acquired medical image and the annotations, wherein the location data is indicative of the position of at least one of the electrodes relative to at least one of the anatomy or at least another one of the electrodes;

reconstruct the representation of the at least one lead including electrodes on an anatomical template image to provide a reconstructed image; and provide to the programming system both the reconstructed image and the location data for use by the programming system to program the neuromodulation device.

2. The method of claim 1, wherein the programming system is configured to use the location data to determine energy contributions for the electrodes.

3. The method of claim 1, wherein the medical imaging system includes a fluoroscopy imaging system and the displayed image is a displayed fluoroscopic image, and the displayed image includes a representation of at least one lead implanted proximate to a spine.

4. The method of claim 3, wherein the acquiring the displayed image includes receiving a clipped image of the picture.

5. The method of claim 1, wherein the mobile device includes a phone.

6. The method of claim 1, wherein the acquired image is a transitory image on the mobile device that is available for annotating the image and determining the location data during a current session but is not retrievably stored on the mobile device for access after the current session.

7. The method of claim 1, wherein the annotations for the acquired image include information identifying at least one of vertebral levels, laterality, lead type, at least one electrode contact, or location information for at least one electrode contact.

8. The method of claim 7, wherein the receiving user input annotating the acquired image includes using adjustable markers to accommodate individual spinal anatomy.

9. The method of claim 7, wherein the receiving user input annotating the acquired image includes using interchangeable right and left markers to indicate laterality.

10. The method of claim 1, wherein receiving user input annotating the acquired image includes at least one of:
   receiving user input annotating an orientation of the anatomy represented in the acquired image, or
   receiving user input annotating at least one label for a feature in the anatomy represented in the acquired image.

11. A non-transitory computer-readable storage medium including instructions, which when executed using at least one processor within a mobile device, cause the mobile device to provide information to a programming system based on a displayed medical image in a medical imaging system, including cause the mobile device to:
   take a picture, using a camera from the mobile device, of the displayed medical image from the medical imaging system, wherein the displayed medical image includes a representation of anatomy and a representation of at least one lead, wherein the at least one lead includes electrodes;
   receive user input annotating the acquired image to provide annotations in an annotated image;
   based on the acquired medical image and the annotations, determine location data indicative of the position of at least one of the electrodes relative to at least one of the anatomy or at least another one of the electrodes; and
   provide to the programming system both the reconstructed image and the location data for use by at least one programming algorithm in the programming system to program the neuromodulation device.

12. The non-transitory computer-readable storage medium of claim 11, wherein the programming system is configured to use the location data to determine energy contributions for the electrodes and program the neuromodulation device according to the determined energy contributions.

13. The non-transitory computer-readable storage medium of claim 11, wherein the annotations include an orientation of the anatomy represented in the acquired image, or at least one label for a feature in the anatomy represented in the acquired image.

14. The non-transitory computer-readable storage medium of claim 13, wherein the mobile device includes a phone, and the picture taken of the displayed image is taken using the phone.

15. The non-transitory computer-readable storage medium of claim 14, wherein the acquired image is a transitory image on the mobile device that is available for annotating the image and determining the location data during a current session but is not retrievably stored on the mobile device for access after the current session.

16. The non-transitory computer-readable storage medium of claim 14, wherein the instructions, which when executed using the at least one processor, cause the phone to receive user input annotating the acquired image to provide the annotated image.

17. The non-transitory computer-readable storage medium of claim 14, wherein the instructions, which when executed using the at least one processor, cause the phone to use the annotated image to provide the reconstructed image.

18. The non-transitory computer-readable storage medium of claim 14, wherein the instructions, which when executed using the at least one processor, cause the phone to use the annotated image to determine location data indicative of the positions of the electrodes and the anatomy.

19. A system for use with a medical imaging system and a programming system, wherein the medical imaging system is configured to display a medical image and the programming system is configured to implement a program used in programming a neuromodulation device, the system comprising a mobile device having at least one processor, a camera and a user interface including a display, wherein the mobile device is configured to provide information to the programming system based on a displayed medical image in the medical imaging system:
   acquire the displayed medical image from the medical imaging system, wherein the acquired image includes an image from a picture taken by the camera of the mobile device, wherein the displayed medical image includes a representation of anatomy and a representation of at least one lead, wherein the at least one lead includes electrodes;
   receive user input annotating the acquired images to provide annotations in an annotated image;
   based on the acquired medical image and the annotations, determine location data indicative of the position of at least one of the electrodes relative to at least one of the anatomy or at least another one of the electrodes; and
   provide to the programming system the location data for use by the program implemented by the programming system, wherein the programming system is configured to use the location data in programming the neuromodulation device.

20. The system of claim 19, wherein the acquired image is a transitory image on the mobile device that is available for annotating the image and determining the location data during a current session but is not retrievably stored on the mobile device for access after the current session.

\* \* \* \* \*